US007598040B2

(12) United States Patent
Guenther et al.

(10) Patent No.: US 7,598,040 B2
(45) Date of Patent: Oct. 6, 2009

(54) COMPOSITIONS AND METHODS FOR THE IDENTIFICATION OF INHIBITORS OF PROTEIN SYNTHESIS

(75) Inventors: Richard H. Guenther, Cary, NC (US); Winnell H. Newman, Cary, NC (US); Samuel P. Yenne, Cary, NC (US); Dan Mitchell, Raleigh, NC (US); Andrzej Malkiewicz, Lodz (PL)

(73) Assignee: Trana Discovery, Inc., Cary, NC (US)

( * ) Notice: Subject to any disclaimer, the term of this patent is extended or adjusted under 35 U.S.C. 154(b) by 68 days.

(21) Appl. No.: 11/943,924

(22) Filed: Nov. 21, 2007

(65) Prior Publication Data

US 2008/0199870 A1 Aug. 21, 2008

Related U.S. Application Data

(60) Provisional application No. 60/866,988, filed on Nov. 22, 2006, provisional application No. 60/867,263, filed on Nov. 27, 2006.

(51) Int. Cl.
*C12Q 1/68* (2006.01)

(52) U.S. Cl. .......................................................... 435/6
(58) Field of Classification Search ....................... None
See application file for complete search history.

(56) References Cited

U.S. PATENT DOCUMENTS

2006/0051771 A1 * 3/2006 Murphy et al. ................. 435/6

* cited by examiner

*Primary Examiner*—James Martinell
(74) *Attorney, Agent, or Firm*—David S. Bradin; Intellectual Property Technology Law

(57) ABSTRACT

Compositions and methods for identifying inhibitors of RNA-target molecule interactions are provided as well as identifying inhibitors that block the role of tRNA in protein synthesis. The methods involve forming a mixture comprising a tRNA fragment molecule containing a modified nucleotide, a target molecule capable of binding to the tRNA fragment, and a test compound. The mixture is incubated under conditions that allow binding of the tRNA and the target molecule in the absence of the test compound. Assays can then be performed that detect whether or not the test compound inhibits the binding of the tRNA molecule and the target molecule. High throughput assays are also provided.

39 Claims, 7 Drawing Sheets

```
                                   10        20        30        40        50        60        70        80        90
                           ....|....|....|....|....|....|....|....|....|....|....|....|....|....|....|....|....|....|
Shigella flexneri          ---------------MSEQHAQGADAVVDLNNELKTRR-EKLANLREQGIA-FPNDFRRDHTSDQLHAEFD-GKENEELEALNIEVAVAG
Escherichia coli           ---------------MSEQHAQGADAVVDLNNELKTRR-EKLANLREQGIA-FPNDFRRDHTSDQLHAEFD-GKENEELEALNIEVAVAG
Salmonella enterica        ---------------MSEQNAQGADEVVDLNNEMKARR-EKLAALREQGIP-FPNDFRRDRTSDQLHAEFD-AKEAEELEALNIEVSVAG
Yersinia enterocolitica    ---------------MSEQKPQVAEQAQELNSELQARR-EKLAVLRGKGIA-FPNDFRRENLSDQLHAEFD-SKENEELEALNIDVTVAG
Listeria monocytogenes     ---------------MSNEN------HEELNDQLIVRR-EKVDTLREEGIDPFGEKFIRSISPEEIETKFA-DKSKEELEEAAIEVSVAG
Campylobacter jejuni       ----------------------------MFDNILEQQRIEKAKELKNLGINPYPHFLEKEMSLKTFKDKFSYILEQVEKRDESVNAVVAG
Vibrio cholerae            ------------------------------------------------------------------------------------------
Homo sapien                VLSSLLLGRALREDGGRAGGRGESGWQRAETEQEAEETPESEESSREGGQTERAQETAKPSHCCCHQPHHWCGSGRERGPKSILQNPQSS

                                  100       110       120       130       140       150       160       170       180
                           ....|....|....|....|....|....|....|....|....|....|....|....|....|....|....|....|....|....|
Shigella flexneri          RMMTRRIMGKASFVTLQD-VGGRIQLYVARDDLPEGVYNEQFKKWDLGDILGAKGKLFKTKTGELSIHCTELRLLTKALRPLPDKFHGLQ
Escherichia coli           RMMTRRIMGKASFVTLQD-VGGRIQLYVARDDLPEGVYNEQFKKWDLGDILGAKGKLFKTKTGELSIHCTELRLLTKALRPLPDKFHGLQ
Salmonella enterica        RMMTRRIMGKASFVTLQD-VGGRIQLYVARDDLPEGVYNEQFKKWDLGDILGAKGKLFKTKTGELSIHCTELRLLTKALRPLPDKFHGLQ
Yersinia enterocolitica    RMMTRRIMGKASFVTLQD-VGGRIQLYVSRDDLPEGVYNEEFKKWDLGDILGARGKLFKTKTGELSIHCSELRLLTKALRPLPDKFHGLA
Listeria monocytogenes     RIMTKRVKGKVGFTHIQD-RFHQLQIYIRKDAIGEDAY-AVFKLADLGDIIGIKGTIFRTNTGELSVKATEFTLLSKSLRPLPDKYHGLK
Campylobacter jejuni       RLKLLRIAGKSIFANIED-EDTNLQIYFSKDSVGEELYTILKKNLEVGDIVLVKGFPFVTKTGEFSLHASEVKLATKAIVPLPEKYHGLT
Vibrio cholerae            ----------MSQLSLAF-CSERVQFVIS-------------------------------------VSCDEPPMTNSDWMPT--------
Homo sapien                NSSAEGQWGRPIPTQVPCRHLTHLHPKISPAAWGSPDHHLKGGRDPCQKSFWGKAHLLSSRRGGEVASHGQFQKLIRRRIYSYQTASGRH
```

FIG. 1A

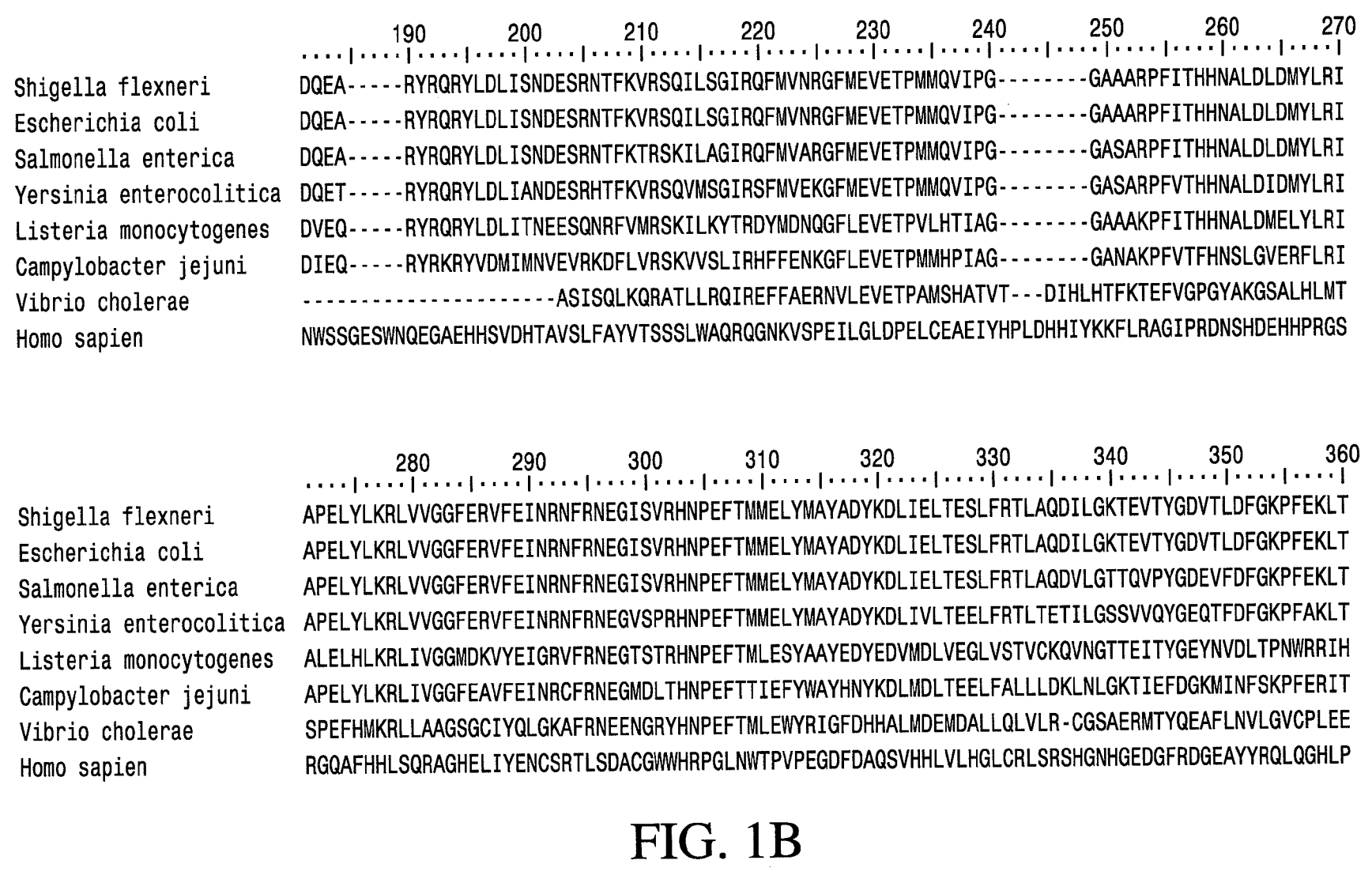

```
                                190       200       210       220       230       240       250       260       270
Shigella flexneri           DQEA-----RYRQRYLDLISNDESRNTFKVRSQILSGIRQFMVNRGFMEVETPMMQVIPG--------GAAARPFITHHNALDLDMYLRI
Escherichia coli            DQEA-----RYRQRYLDLISNDESRNTFKVRSQILSGIRQFMVNRGFMEVETPMMQVIPG--------GAAARPFITHHNALDLDMYLRI
Salmonella enterica         DQEA-----RYRQRYLDLISNDESRNTFKTRSKILAGIRQFMVARGFMEVETPMMQVIPG--------GASARPFITHHNALDLDMYLRI
Yersinia enterocolitica     DQET-----RYRQRYLDLIANDESRHTFKVRSQVMSGIRSFMVEKGFMEVETPMMQVIPG--------GASARPFVTHHNALDIDMYLRI
Listeria monocytogenes      DVEQ-----RYRQRYLDLITNEESQNRFVMRSKILKYTRDYMDNQGFLEVETPVLHTIAG--------GAAAKPFITHHNALDMELYLRI
Campylobacter jejuni        DIEQ-----RYRKRYVDMIMNVEVRKDFLVRSKVVSLIRHFFENKGFLEVETPMMHPIAG--------GANAKPFVTFHNSLGVERFLRI
Vibrio cholerae             ----------------------ASISQLKQRATLLRQIREFFAERNVLEVETPAMSHATVT---DIHLHTFKTEFVGPGYAKGSALHLMT
Homo sapien                 NWSSGESWNQEGAEHHSVDHTAVSLFAYVTSSSLWAQRQGNKVSPEILGLDPELCEAEIYHPLDHHIYKKFLRAGIPRDNSHDEHHPRGS

                                280       290       300       310       320       330       340       350       360
Shigella flexneri           APELYLKRLVVGGFERVFEINRNFRNEGISVRHNPEFTMMELYMAYADYKDLIELTESLFRTLAQDILGKTEVTYGDVTLDFGKPFEKLT
Escherichia coli            APELYLKRLVVGGFERVFEINRNFRNEGISVRHNPEFTMMELYMAYADYKDLIELTESLFRTLAQDILGKTEVTYGDVTLDFGKPFEKLT
Salmonella enterica         APELYLKRLVVGGFERVFEINRNFRNEGISVRHNPEFTMMELYMAYADYKDLIELTESLFRTLAQDVLGTTQVPYGDEVFDFGKPFEKLT
Yersinia enterocolitica     APELYLKRLVVGGFERVFEINRNFRNEGVSPRHNPEFTMMELYMAYADYKDLIVLTEELFRTLTETILGSSVVQYGEQTFDFGKPFAKLT
Listeria monocytogenes      ALELHLKRLIVGGMDKVYEIGRVFRNEGTSTRHNPEFTMLESYAAYEDYEDVMDLVEGLVSTVCKQVNGTTEITYGEYNVDLTPNWRRIH
Campylobacter jejuni        APELYLKRLIVGGFEAVFEINRCFRNEGMDLTHNPEFTTIEFYWAYHNYKDLMDLTEELFALLLDKLNLGKTIEFDGKMINFSKPFERIT
Vibrio cholerae             SPEFHMKRLLAAGSGCIYQLGKAFRNEENGRYHNPEFTMLEWYRIGFDHHALMDEMDALLQLVLR-CGSAERMTYQEAFLNVLGVCPLEE
Homo sapien                 RGQAFHHLSQRAGHELIYENCSRTLSDACGWWHRPGLNWTPVPEGDFDAQSVHHLVLHGLCRLSRSHGNHGEDGFRDGEAYYRQLQGHLP
```

FIG. 1B

```
                          370       380       390       400       410       420       430       440       450
                      ....|....|....|....|....|....|....|....|....|....|....|....|....|....|....|....|....|....|
Shigella flexneri        ----MREAIKKYRPETDMADLDNFDSAKAIAESIGIHVEKSWGLGRIVTEIFEEVAEAHLIQPTFITEYP--------AEVSPLARR--N
Escherichia coli         ----MREAIKKYRPETDMADLDNFDSAKAIAESIGIHVEKSWGLGRIVTEIFEEVAEAHLIQPTFITEYP--------AEVSPLARR--N
Salmonella enterica      ----MREAIKKYRPETDMADLDNFDSAKAIAESIGIHVEKSWGLGRIVTEIFDEVAEAHLIQPTFITEYP--------AEVSPLARR--N
Yersinia enterocolitica  ----MKEAICKYRPETNVADLDDMDKAVAIAESLGIKVEKSWGLGRIQCEIFEETAESHLIQPTFITEYP--------AEVSPLARR--N
Listeria monocytogenes   ----MADAVKEY-VGVDFWNVTSDEEARELAKKHNVPVTEHMTYGHILNEFFETYVEEKLIQPTFVYGHP--------VEISPLAKK--N
Campylobacter jejuni     ----YKDALCKY-GGLDRDLIEDKEKILTKLKADGFEANEKLELGHLQAELFDNYVEEKLINPTFVIDFP--------ISISPLSRR--S
Vibrio cholerae          ----EMRELKQVAATLGLSDIAEPEEDRDTLLQLLFSIGIEPKIG-------------QITPAFVYDFP--------ASQAALAKI--N
Homo sapien              PRWPRGPSLRCLHPTLPANQHGRRAESPGDEAARNEPLNRNSQNSYLCGKSCMPSTSDHSQAPQACWGVPGSDLHQSYIHLSPTDNEPFG

                          460       470       480       490       500       510       520       530       540
                      ....|....|....|....|....|....|....|....|....|....|....|....|....|....|....|....|....|
Shigella flexneri        DINPEITDRFEFFIGGREIGNGFSELNDAEDQAQRFLDQVAAKDAG-----------DDEAMFYDEDYVTALEHGLPPTAG---------
Escherichia coli         DVNPEITDRFEFFIGGREIGNGFSELNDAEDQAQRFLDQVAAKDAG-----------DDEAMFYDEDYVTALEHGLPPTAG---------
Salmonella enterica      DVNPEITDRFEFFIGGREIGNGFSELNDAEDQAQRFLDQVNAKAAG-----------DDEAMFYDEDYVTALEHGLPPTAG---------
Yersinia enterocolitica  DDNPFITDRFEFFIGGREIGNGFSELNDAEDQAQRFADQVSAKEAG-----------DDEAMFYDEDYITALEHGLPPTAG---------
Listeria monocytogenes   KEDDRFTDRFELFIVGREHANAFSELNDPIDQRERFEAQMKEREQG-----------NDEAHGMDADFLEALEYGLPPTGG---------
Campylobacter jejuni     DEDSQIAERFELFICGRELANGFNELNDPLDQYERFLKQIEAKNAG-----------DEEACEMDEDFVNALGYGMPPTAG---------
Vibrio cholerae          PADPRVADRFEVYFKGIELANGFHELDNPAEQLARFKADNAKRLEM-----------GLTEQPIDYHLIAALEAGLPECAG---------
Homo sapien              MAPLRGSDALAVCHEERDMQCVYAESHAAAAAFRTGQGQGCRGHVHRKLLYCPGIWAAPHSWLGHGHSSRHVSHGLQQHQGSTSVSCHET
```

FIG. 1C

```
                               550       560       570       580       590       600       610
                           ....|....|....|....|....|....|....|....|....|....|....|....|....|....|....|
Shigella flexneri          -----------LGIGIDRMVMLFTNSHTIRDVILFPAMRPVK---------------------------------
Escherichia coli           -----------LGIGIDRMVMLFTNSHTIRDVILFPAMRPVK---------------------------------
Salmonella enterica        -----------LGIGIDRMVMLFTNSHTIRDVILFPAMRPVK---------------------------------
Yersinia enterocolitica    -----------LGIGIDRMVMLFTNSHTIRDVILFPAMRPVK---------------------------------
Listeria monocytogenes     -----------LGIGIDRLVMLLTDAPSIRDILLFPTMKHRD---------------------------------
Campylobacter jejuni       -----------QGIGIDRLVMLLTNKKSIRDVILFPAMRPLKSELKEKE--------------------------
Vibrio cholerae            -----------VALGIDRLIMLALGEDHIDKVTAFPFPRA-----------------------------------
Homo sapien                RRQEGECSNHYTGKHNSWHFCLENNNCKLYNSGVFAFLRKIKVCKGILVCCFPFDTAVLFSHQKRDKELKISFSC
```

FIG. 1D

| Motif 1 | Position 8 | Position 11 | Position 13 | |
|---|---|---|---|---|
| | cmo5U | T6A | Psi | |
| | cmnm5U | m2A | | |
| | mnm5s2U | ms2t6A | | |
| | Gm | m6A | | |
| | Q | ms2i6A | | |
| | k2C | m1G | | |
| | cmnm5s2U | i6A | | |
| | Cm | fa7d7G | | |
| | cmnm5Um | m1I | | |
| | Ac4c | Y | | |
| | I | cmnm5Um | | |
| | m5C | m1G | | |
| | Um | | | |
| | mcm5s2Um | | | |
| | ncm5s2Um | | | |
| | s2U | | | |
| | manQ | | | |
| | | | | |
| **Motif 2** | **Position 1** | **Position 6** | **Position 7** | **Position 10** |
| | m5C | T | Psi | m1A |
| | | | | |
| **Motif 3** | **Position 1** | **Position 8** | **Position 10** | |
| | m2G | D | X | |
| | | m1A | | |

SEQUENCE LISTING

<160> NUMBER OF SEQ ID NOS: 21

<210> SEQ ID NO 1
<211> LENGTH: 505
<212> TYPE: PRT
<213> ORGANISM: Shigella flexneri

<400> SEQUENCE: 1

Met Ser Glu Gln His Ala Gln Gly Ala Asp Ala Val Val Asp Leu Asn
1 5 10 15

Asn Glu Leu Lys Thr Arg Arg Glu Lys Leu Ala Asn Leu Arg Glu Gln
20 25 30

Gly Ile Ala Phe Pro Asn Asp Phe Arg Arg Asp His Thr Ser Asp Gln
35 40 45

Leu His Ala Glu Phe Asp Gly Lys Glu Asn Glu Glu Leu Glu Ala Leu
50 55 60

Asn Ile Glu Val Ala Val Ala Gly Arg Met Met Thr Arg Arg Ile Met
65 70 75 80

Gly Lys Ala Ser Phe Val Thr Leu Gln Asp Val Gly Gly Arg Ile Gln
85 90 95

Leu Tyr Val Ala Arg Asp Asp Leu Pro Glu Gly Val Tyr Asn Glu Gln
100 105 110

Phe Lys Lys Trp Asp Leu Gly Asp Ile Leu Gly Ala Lys Gly Lys Leu
115 120 125

Phe Lys Thr Lys Thr Gly Glu Leu Ser Ile His Cys Thr Glu Leu Arg
130 135 140

Leu Leu Thr Lys Ala Leu Arg Pro Leu Pro Asp Lys Phe His Gly Leu
145 150 155 160

Gln Asp Gln Glu Ala Arg Tyr Arg Gln Arg Tyr Leu Asp Leu Ile Ser
165 170 175

Asn Asp Glu Ser Arg Asn Thr Phe Lys Val Arg Ser Gln Ile Leu Ser
180 185 190

Gly Ile Arg Gln Phe Met Val Asn Arg Gly Phe Met Glu Val Glu Thr
195 200 205

Pro Met Met Gln Val Ile Pro Gly Gly Ala Ala Ala Arg Pro Phe Ile
210 215 220

-continued

Thr His His Asn Ala Leu Asp Leu Asp Met Tyr Leu Arg Ile Ala Pro
225 230 235 240

Glu Leu Tyr Leu Lys Arg Leu Val Val Gly Gly Phe Glu Arg Val Phe
245 250 255

Glu Ile Asn Arg Asn Phe Arg Asn Glu Gly Ile Ser Val Arg His Asn
260 265 270

Pro Glu Phe Thr Met Met Glu Leu Tyr Met Ala Tyr Ala Asp Tyr Lys
275 280 285

Asp Leu Ile Glu Leu Thr Glu Ser Leu Phe Arg Thr Leu Ala Gln Asp
290 295 300

Ile Leu Gly Lys Thr Glu Val Thr Tyr Gly Asp Val Thr Leu Asp Phe
305 310 315 320

Gly Lys Pro Phe Glu Lys Leu Thr Met Arg Glu Ala Ile Lys Lys Tyr
325 330 335

Arg Pro Glu Thr Asp Met Ala Asp Leu Asp Asn Phe Asp Ser Ala Lys
340 345 350

Ala Ile Ala Glu Ser Ile Gly Ile His Val Glu Lys Ser Trp Gly Leu
355 360 365

Gly Arg Ile Val Thr Glu Ile Phe Glu Glu Val Ala Glu Ala His Leu
370 375 380

Ile Gln Pro Thr Phe Ile Thr Glu Tyr Pro Ala Glu Val Ser Pro Leu
385 390 395 400

Ala Arg Arg Asn Asp Ile Asn Pro Glu Ile Thr Asp Arg Phe Glu Phe
405 410 415

Phe Ile Gly Gly Arg Glu Ile Gly Asn Gly Phe Ser Glu Leu Asn Asp
420 425 430

Ala Glu Asp Gln Ala Gln Arg Phe Leu Asp Gln Val Ala Ala Lys Asp
435 440 445

Ala Gly Asp Asp Glu Ala Met Phe Tyr Asp Glu Asp Tyr Val Thr Ala
450 455 460

Leu Glu His Gly Leu Pro Pro Thr Ala Gly Leu Gly Ile Gly Ile Asp
465 470 475 480

Arg Met Val Met Leu Phe Thr Asn Ser His Thr Ile Arg Asp Val Ile
485 490 495

Leu Phe Pro Ala Met Arg Pro Val Lys
500 505

<210> SEQ ID NO 2
<211> LENGTH: 505
<212> TYPE: PRT
<213> ORGANISM: Escherichia coli

<400> SEQUENCE: 2

Met Ser Glu Gln His Ala Gln Gly Ala Asp Ala Val Val Asp Leu Asn
1 5 10 15

Asn Glu Leu Lys Thr Arg Arg Glu Lys Leu Ala Asn Leu Arg Glu Gln
20 25 30

Gly Ile Ala Phe Pro Asn Asp Phe Arg Arg Asp His Thr Ser Asp Gln
35 40 45

Leu His Ala Glu Phe Asp Gly Lys Glu Asn Glu Glu Leu Glu Ala Leu
50 55 60

Asn Ile Glu Val Ala Val Ala Gly Arg Met Met Thr Arg Arg Ile Met
65 70 75 80

Gly Lys Ala Ser Phe Val Thr Leu Gln Asp Val Gly Gly Arg Ile Gln
85 90 95

-continued

```
Leu Tyr Val Ala Arg Asp Asp Leu Pro Glu Gly Val Tyr Asn Glu Gln
100                 105                 110

Phe Lys Lys Trp Asp Leu Gly Asp Ile Leu Gly Ala Lys Gly Lys Leu
115                 120                 125

Phe Lys Thr Lys Thr Gly Glu Leu Ser Ile His Cys Thr Glu Leu Arg
130                 135                 140

Leu Leu Thr Lys Ala Leu Arg Pro Leu Pro Asp Lys Phe His Gly Leu
145                 150                 155                 160

Gln Asp Gln Glu Ala Arg Tyr Arg Gln Arg Tyr Leu Asp Leu Ile Ser
165                 170                 175

Asn Asp Glu Ser Arg Asn Thr Phe Lys Val Arg Ser Gln Ile Leu Ser
180                 185                 190

Gly Ile Arg Gln Phe Met Val Asn Arg Gly Phe Met Glu Val Glu Thr
195                 200                 205

Pro Met Met Gln Val Ile Pro Gly Gly Ala Ala Ala Arg Pro Phe Ile
210                 215                 220

Thr His His Asn Ala Leu Asp Leu Asp Met Tyr Leu Arg Ile Ala Pro
225                 230                 235                 240

Glu Leu Tyr Leu Lys Arg Leu Val Val Gly Gly Phe Glu Arg Val Phe
245                 250                 255

Glu Ile Asn Arg Asn Phe Arg Asn Glu Gly Ile Ser Val Arg His Asn
260                 265                 270

Pro Glu Phe Thr Met Met Glu Leu Tyr Met Ala Tyr Ala Asp Tyr Lys
275                 280                 285

Asp Leu Ile Glu Leu Thr Glu Ser Leu Phe Arg Thr Leu Ala Gln Asp
290                 295                 300

Ile Leu Gly Lys Thr Glu Val Thr Tyr Gly Asp Val Thr Leu Asp Phe
305                 310                 315                 320

Gly Lys Pro Phe Glu Lys Leu Thr Met Arg Glu Ala Ile Lys Lys Tyr
325                 330                 335

Arg Pro Glu Thr Asp Met Ala Asp Leu Asp Asn Phe Asp Ser Ala Lys
340                 345                 350

Ala Ile Ala Glu Ser Ile Gly Ile His Val Glu Lys Ser Trp Gly Leu
355                 360                 365

Gly Arg Ile Val Thr Glu Ile Phe Glu Glu Val Ala Glu Ala His Leu
370                 375                 380

Ile Gln Pro Thr Phe Ile Thr Glu Tyr Pro Ala Glu Val Ser Pro Leu
385                 390                 395                 400

Ala Arg Arg Asn Asp Val Asn Pro Glu Ile Thr Asp Arg Phe Glu Phe
405                 410                 415

Phe Ile Gly Gly Arg Glu Ile Gly Asn Gly Phe Ser Glu Leu Asn Asp
420                 425                 430

Ala Glu Asp Gln Ala Gln Arg Phe Leu Asp Gln Val Ala Ala Lys Asp
435                 440                 445

Ala Gly Asp Asp Glu Ala Met Phe Tyr Asp Glu Asp Tyr Val Thr Ala
450                 455                 460

Leu Glu His Gly Leu Pro Pro Thr Ala Gly Leu Gly Ile Gly Ile Asp
465                 470                 475                 480

Arg Met Val Met Leu Phe Thr Asn Ser His Thr Ile Arg Asp Val Ile
485                 490                 495

Leu Phe Pro Ala Met Arg Pro Val Lys
500                 505
```

-continued

<210> SEQ ID NO 3
<211> LENGTH: 505
<212> TYPE: PRT
<213> ORGANISM: Salmonella enterica

<400> SEQUENCE: 3

Met Ser Glu Gln Asn Ala Gln Gly Ala Asp Glu Val Val Asp Leu Asn
1               5                   10                  15

Asn Glu Met Lys Ala Arg Arg Glu Lys Leu Ala Ala Leu Arg Glu Gln
20                  25                  30

Gly Ile Pro Phe Pro Asn Asp Phe Arg Arg Asp Arg Thr Ser Asp Gln
35                  40                  45

Leu His Ala Glu Phe Asp Ala Lys Glu Ala Glu Glu Leu Glu Ala Leu
50                  55                  60

Asn Ile Glu Val Ser Val Ala Gly Arg Met Met Thr Arg Arg Ile Met
65                  70                  75                  80

Gly Lys Ala Ser Phe Val Thr Leu Gln Asp Val Gly Gly Arg Ile Gln
85                  90                  95

Leu Tyr Val Ala Arg Asp Asp Leu Pro Glu Gly Val Tyr Asn Glu Gln
100                 105                 110

Phe Lys Lys Trp Asp Leu Gly Asp Ile Leu Gly Ala Lys Gly Lys Leu
115                 120                 125

Phe Lys Thr Lys Thr Gly Glu Leu Ser Ile His Cys Thr Glu Leu Arg
130                 135                 140

Leu Leu Thr Lys Ala Leu Arg Pro Leu Pro Asp Lys Phe His Gly Leu
145                 150                 155                 160

Gln Asp Gln Glu Ala Arg Tyr Arg Gln Arg Tyr Leu Asp Leu Ile Ser
165                 170                 175

Asn Asp Glu Ser Arg Asn Thr Phe Lys Thr Arg Ser Lys Ile Leu Ala
180                 185                 190

Gly Ile Arg Gln Phe Met Val Ala Arg Gly Phe Met Glu Val Glu Thr
195                 200                 205

Pro Met Met Gln Val Ile Pro Gly Gly Ala Ser Ala Arg Pro Phe Ile
210                 215                 220

Thr His His Asn Ala Leu Asp Leu Asp Met Tyr Leu Arg Ile Ala Pro
225                 230                 235                 240

Glu Leu Tyr Leu Lys Arg Leu Val Val Gly Gly Phe Glu Arg Val Phe
245                 250                 255

Glu Ile Asn Arg Asn Phe Arg Asn Glu Gly Ile Ser Val Arg His Asn
260                 265                 270

Pro Glu Phe Thr Met Met Glu Leu Tyr Met Ala Tyr Ala Asp Tyr Lys
275                 280                 285

Asp Leu Ile Glu Leu Thr Glu Ser Leu Phe Arg Thr Leu Ala Gln Asp
290                 295                 300

Val Leu Gly Thr Thr Gln Val Pro Tyr Gly Asp Glu Val Phe Asp Phe
305                 310                 315                 320

Gly Lys Pro Phe Glu Lys Leu Thr Met Arg Glu Ala Ile Lys Lys Tyr
325                 330                 335

Arg Pro Glu Thr Asp Met Ala Asp Leu Asp Asn Phe Asp Ser Ala Lys
340                 345                 350

Ala Ile Ala Glu Ser Ile Gly Ile His Val Glu Lys Ser Trp Gly Leu
355                 360                 365

Gly Arg Ile Val Thr Glu Ile Phe Asp Glu Val Ala Glu Ala His Leu
370                 375                 380

-continued

Ile Gln Pro Thr Phe Ile Thr Glu Tyr Pro Ala Glu Val Ser Pro Leu
385 390 395 400

Ala Arg Arg Asn Asp Val Asn Pro Glu Ile Thr Asp Arg Phe Glu Phe
405 410 415

Phe Ile Gly Gly Arg Glu Ile Gly Asn Gly Phe Ser Glu Leu Asn Asp
420 425 430

Ala Glu Asp Gln Ala Gln Arg Phe Leu Asp Gln Val Asn Ala Lys Ala
435 440 445

Ala Gly Asp Asp Glu Ala Met Phe Tyr Asp Glu Asp Tyr Val Thr Ala
450 455 460

Leu Glu His Gly Leu Pro Pro Thr Ala Gly Leu Gly Ile Gly Ile Asp
465 470 475 480

Arg Met Val Met Leu Phe Thr Asn Ser His Thr Ile Arg Asp Val Ile
485 490 495

Leu Phe Pro Ala Met Arg Pro Val Lys
500 505

<210> SEQ ID NO 4
<211> LENGTH: 505
<212> TYPE: PRT
<213> ORGANISM: Yersinia enterocolitica

<400> SEQUENCE: 4

Met Ser Glu Gln Lys Pro Gln Val Ala Glu Gln Ala Gln Glu Leu Asn
1 5 10 15

Ser Glu Leu Gln Ala Arg Arg Glu Lys Leu Ala Val Leu Arg Gly Lys
20 25 30

Gly Ile Ala Phe Pro Asn Asp Phe Arg Arg Glu Asn Leu Ser Asp Gln
35 40 45

Leu His Ala Glu Phe Asp Ser Lys Glu Asn Glu Glu Leu Glu Ala Leu
50 55 60

Asn Ile Asp Val Thr Val Ala Gly Arg Met Met Thr Arg Arg Ile Met
65 70 75 80

Gly Lys Ala Ser Phe Val Thr Leu Gln Asp Val Gly Gly Arg Ile Gln
85 90 95

Leu Tyr Val Ser Arg Asp Asp Leu Pro Glu Gly Val Tyr Asn Glu Glu
100 105 110

Phe Lys Lys Trp Asp Leu Gly Asp Ile Leu Gly Ala Arg Gly Lys Leu
115 120 125

Phe Lys Thr Lys Thr Gly Glu Leu Ser Ile His Cys Ser Glu Leu Arg
130 135 140

Leu Leu Thr Lys Ala Leu Arg Pro Leu Pro Asp Lys Phe His Gly Leu
145 150 155 160

Ala Asp Gln Glu Thr Arg Tyr Arg Gln Arg Tyr Leu Asp Leu Ile Ala
165 170 175

Asn Asp Glu Ser Arg His Thr Phe Lys Val Arg Ser Gln Val Met Ser
180 185 190

Gly Ile Arg Ser Phe Met Val Glu Lys Gly Phe Met Glu Val Glu Thr
195 200 205

Pro Met Met Gln Val Ile Pro Gly Gly Ala Ser Ala Arg Pro Phe Val
210 215 220

Thr His His Asn Ala Leu Asp Ile Asp Met Tyr Leu Arg Ile Ala Pro
225 230 235 240

Glu Leu Tyr Leu Lys Arg Leu Val Val Gly Gly Phe Glu Arg Val Phe

-continued 245 250 255

Glu Ile Asn Arg Asn Phe Arg Asn Glu Gly Val Ser Pro Arg His Asn
260 265 270

Pro Glu Phe Thr Met Met Glu Leu Tyr Met Ala Tyr Ala Asp Tyr Lys
275 280 285

Asp Leu Ile Val Leu Thr Glu Glu Leu Phe Arg Thr Leu Thr Glu Thr
290 295 300

Ile Leu Gly Ser Ser Val Val Gln Tyr Gly Glu Gln Thr Phe Asp Phe
305 310 315 320

Gly Lys Pro Phe Ala Lys Leu Thr Met Lys Glu Ala Ile Cys Lys Tyr
325 330 335

Arg Pro Glu Thr Asn Val Ala Asp Leu Asp Asp Met Asp Lys Ala Val
340 345 350

Ala Ile Ala Glu Ser Leu Gly Ile Lys Val Glu Lys Ser Trp Gly Leu
355 360 365

Gly Arg Ile Gln Cys Glu Ile Phe Glu Glu Thr Ala Glu Ser His Leu
370 375 380

Ile Gln Pro Thr Phe Ile Thr Glu Tyr Pro Ala Glu Val Ser Pro Leu
385 390 395 400

Ala Arg Arg Asn Asp Asp Asn Pro Phe Ile Thr Asp Arg Phe Glu Phe
405 410 415

Phe Ile Gly Gly Arg Glu Ile Gly Asn Gly Phe Ser Glu Leu Asn Asp
420 425 430

Ala Glu Asp Gln Ala Gln Arg Phe Ala Asp Gln Val Ser Ala Lys Glu
435 440 445

Ala Gly Asp Asp Glu Ala Met Phe Tyr Asp Glu Asp Tyr Ile Thr Ala
450 455 460

Leu Glu His Gly Leu Pro Pro Thr Ala Gly Leu Gly Ile Gly Ile Asp
465 470 475 480

Arg Met Val Met Leu Phe Thr Asn Ser His Thr Ile Arg Asp Val Ile
485 490 495

Leu Phe Pro Ala Met Arg Pro Val Lys
500 505

<210> SEQ ID NO 5
<211> LENGTH: 498
<212> TYPE: PRT
<213> ORGANISM: Listeria monocytogenes

<400> SEQUENCE: 5

Met Ser Asn Glu Asn His Glu Glu Leu Asn Asp Gln Leu Ile Val Arg
1 5 10 15

Arg Glu Lys Val Asp Thr Leu Arg Glu Glu Gly Ile Asp Pro Phe Gly
20 25 30

Glu Lys Phe Ile Arg Ser Ile Ser Pro Glu Glu Ile Glu Thr Lys Phe
35 40 45

Ala Asp Lys Ser Lys Glu Glu Leu Glu Glu Ala Ala Ile Glu Val Ser
50 55 60

Val Ala Gly Arg Ile Met Thr Lys Arg Val Lys Gly Lys Val Gly Phe
65 70 75 80

Thr His Ile Gln Asp Arg Phe His Gln Leu Gln Ile Tyr Ile Arg Lys
85 90 95

Asp Ala Ile Gly Glu Asp Ala Tyr Ala Val Phe Lys Leu Ala Asp Leu
100 105 110

-continued

Gly Asp Ile Ile Gly Ile Lys Gly Thr Ile Phe Arg Thr Asn Thr Gly
115 120 125

Glu Leu Ser Val Lys Ala Thr Glu Phe Thr Leu Leu Ser Lys Ser Leu
130 135 140

Arg Pro Leu Pro Asp Lys Tyr His Gly Leu Lys Asp Val Glu Gln Arg
145 150 155 160

Tyr Arg Gln Arg Tyr Leu Asp Leu Ile Thr Asn Glu Glu Ser Gln Asn
165 170 175

Arg Phe Val Met Arg Ser Lys Ile Leu Lys Tyr Thr Arg Asp Tyr Met
180 185 190

Asp Asn Gln Gly Phe Leu Glu Val Glu Thr Pro Val Leu His Thr Ile
195 200 205

Ala Gly Gly Ala Ala Ala Lys Pro Phe Ile Thr His His Asn Ala Leu
210 215 220

Asp Met Glu Leu Tyr Leu Arg Ile Ala Leu Glu Leu His Leu Lys Arg
225 230 235 240

Leu Ile Val Gly Gly Met Asp Lys Val Tyr Glu Ile Gly Arg Val Phe
245 250 255

Arg Asn Glu Gly Thr Ser Thr Arg His Asn Pro Glu Phe Thr Met Leu
260 265 270

Glu Ser Tyr Ala Ala Tyr Glu Asp Tyr Glu Asp Val Met Asp Leu Val
275 280 285

Glu Gly Leu Val Ser Thr Val Cys Lys Gln Val Asn Gly Thr Thr Glu
290 295 300

Ile Thr Tyr Gly Glu Tyr Asn Val Asp Leu Thr Pro Asn Trp Arg Arg
305 310 315 320

Ile His Met Ala Asp Ala Val Lys Glu Tyr Val Gly Val Asp Phe Trp
325 330 335

Asn Val Thr Ser Asp Glu Glu Ala Arg Glu Leu Ala Lys Lys His Asn
340 345 350

Val Pro Val Thr Glu His Met Thr Tyr Gly His Ile Leu Asn Glu Phe
355 360 365

Phe Glu Thr Tyr Val Glu Glu Lys Leu Ile Gln Pro Thr Phe Val Tyr
370 375 380

Gly His Pro Val Glu Ile Ser Pro Leu Ala Lys Lys Asn Lys Glu Asp
385 390 395 400

Asp Arg Phe Thr Asp Arg Phe Glu Leu Phe Ile Val Gly Arg Glu His
405 410 415

Ala Asn Ala Phe Ser Glu Leu Asn Asp Pro Ile Asp Gln Arg Glu Arg
420 425 430

Phe Glu Ala Gln Met Lys Glu Arg Glu Gln Gly Asn Asp Glu Ala His
435 440 445

Gly Met Asp Ala Asp Phe Leu Glu Ala Leu Glu Tyr Gly Leu Pro Pro
450 455 460

Thr Gly Gly Leu Gly Ile Gly Ile Asp Arg Leu Val Met Leu Leu Thr
465 470 475 480

Asp Ala Pro Ser Ile Arg Asp Ile Leu Leu Phe Pro Thr Met Lys His
485 490 495

Arg Asp

<210> SEQ ID NO 6
<211> LENGTH: 501
<212> TYPE: PRT
<213> ORGANISM: Campylobacter jejuni -continued

<400> SEQUENCE: 6

Met Phe Asp Asn Ile Leu Glu Gln Gln Arg Ile Glu Lys Ala Lys Glu
1               5                   10                  15

Leu Lys Asn Leu Gly Ile Asn Pro Tyr Pro His Phe Leu Glu Lys Glu
20                  25                  30

Met Ser Leu Lys Thr Phe Lys Asp Lys Phe Ser Tyr Ile Leu Glu Gln
35                  40                  45

Val Glu Lys Arg Asp Glu Ser Val Asn Ala Val Val Ala Gly Arg Leu
50                  55                  60

Lys Leu Leu Arg Ile Ala Gly Lys Ser Ile Phe Ala Asn Ile Glu Asp
65                  70                  75                  80

Glu Asp Thr Asn Leu Gln Ile Tyr Phe Ser Lys Asp Ser Val Gly Glu
85                  90                  95

Glu Leu Tyr Thr Ile Leu Lys Lys Asn Leu Glu Val Gly Asp Ile Val
100                 105                 110

Leu Val Lys Gly Phe Pro Phe Val Thr Lys Thr Gly Glu Phe Ser Leu
115                 120                 125

His Ala Ser Glu Val Lys Leu Ala Thr Lys Ala Ile Val Pro Leu Pro
130                 135                 140

Glu Lys Tyr His Gly Leu Thr Asp Ile Glu Gln Arg Tyr Arg Lys Arg
145                 150                 155                 160

Tyr Val Asp Met Ile Met Asn Val Glu Val Arg Lys Asp Phe Leu Val
165                 170                 175

Arg Ser Lys Val Val Ser Leu Ile Arg His Phe Phe Glu Asn Lys Gly
180                 185                 190

Phe Leu Glu Val Glu Thr Pro Met Met His Pro Ile Ala Gly Gly Ala
195                 200                 205

Asn Ala Lys Pro Phe Val Thr Phe His Asn Ser Leu Gly Val Glu Arg
210                 215                 220

Phe Leu Arg Ile Ala Pro Glu Leu Tyr Leu Lys Arg Leu Ile Val Gly
225                 230                 235                 240

Gly Phe Glu Ala Val Phe Glu Ile Asn Arg Cys Phe Arg Asn Glu Gly
245                 250                 255

Met Asp Leu Thr His Asn Pro Glu Phe Thr Thr Ile Glu Phe Tyr Trp
260                 265                 270

Ala Tyr His Asn Tyr Lys Asp Leu Met Asp Leu Thr Glu Glu Leu Phe
275                 280                 285

Ala Leu Leu Leu Asp Lys Leu Asn Leu Gly Lys Thr Ile Glu Phe Asp
290                 295                 300

Gly Lys Met Ile Asn Phe Ser Lys Pro Phe Glu Arg Ile Thr Tyr Lys
305                 310                 315                 320

Asp Ala Leu Cys Lys Tyr Gly Gly Leu Asp Arg Asp Leu Ile Glu Asp
325                 330                 335

Lys Glu Lys Ile Leu Thr Lys Leu Lys Ala Asp Gly Phe Glu Ala Asn
340                 345                 350

Glu Lys Leu Glu Leu Gly His Leu Gln Ala Glu Leu Phe Asp Asn Tyr
355                 360                 365

Val Glu Glu Lys Leu Ile Asn Pro Thr Phe Val Ile Asp Phe Pro Ile
370                 375                 380

Ser Ile Ser Pro Leu Ser Arg Arg Ser Asp Glu Asp Ser Gln Ile Ala
385                 390                 395                 400

Glu Arg Phe Glu Leu Phe Ile Cys Gly Arg Glu Leu Ala Asn Gly Phe

-continued 405 410 415

Asn Glu Leu Asn Asp Pro Leu Asp Gln Tyr Glu Arg Phe Leu Lys Gln
420 425 430

Ile Glu Ala Lys Asn Ala Gly Asp Glu Glu Ala Cys Glu Met Asp Glu
435 440 445

Asp Phe Val Asn Ala Leu Gly Tyr Gly Met Pro Pro Thr Ala Gly Gln
450 455 460

Gly Ile Gly Ile Asp Arg Leu Val Met Leu Leu Thr Asn Lys Lys Ser
465 470 475 480

Ile Arg Asp Val Ile Leu Phe Pro Ala Met Arg Pro Leu Lys Ser Glu
485 490 495

Leu Lys Glu Lys Glu
500

<210> SEQ ID NO 7
<211> LENGTH: 348
<212> TYPE: PRT
<213> ORGANISM: Vibrio cholerae

<400> SEQUENCE: 7

Met Ser Gln Leu Ser Leu Ala Phe Cys Ser Glu Arg Val Gln Phe Val
1 5 10 15

Ile Ser Val Ser Cys Asp Glu Pro Pro Met Thr Asn Ser Asp Trp Met
20 25 30

Pro Thr Ala Ser Ile Ser Gln Leu Lys Gln Arg Ala Thr Leu Leu Arg
35 40 45

Gln Ile Arg Glu Phe Phe Ala Glu Arg Asn Val Leu Glu Val Glu Thr
50 55 60

Pro Ala Met Ser His Ala Thr Val Thr Asp Ile His Leu His Thr Phe
65 70 75 80

Lys Thr Glu Phe Val Gly Pro Gly Tyr Ala Lys Gly Ser Ala Leu His
85 90 95

Leu Met Thr Ser Pro Glu Phe His Met Lys Arg Leu Leu Ala Ala Gly
100 105 110

Ser Gly Cys Ile Tyr Gln Leu Gly Lys Ala Phe Arg Asn Glu Glu Asn
115 120 125

Gly Arg Tyr His Asn Pro Glu Phe Thr Met Leu Glu Trp Tyr Arg Ile
130 135 140

Gly Phe Asp His His Ala Leu Met Asp Glu Met Asp Ala Leu Leu Gln
145 150 155 160

Leu Val Leu Arg Cys Gly Ser Ala Glu Arg Met Thr Tyr Gln Glu Ala
165 170 175

Phe Leu Asn Val Leu Gly Val Cys Pro Leu Glu Glu Glu Met Arg Glu
180 185 190

Leu Lys Gln Val Ala Ala Thr Leu Gly Leu Ser Asp Ile Ala Glu Pro
195 200 205

Glu Glu Asp Arg Thr Leu Leu Gln Leu Leu Phe Ser Ile Gly Ile Glu
210 215 220

Pro Lys Ile Gly Gln Ile Thr Pro Ala Phe Val Tyr Asp Phe Pro Ala
225 230 235 240

Ser Gln Ala Ala Leu Ala Lys Ile Asn Pro Ala Asp Pro Arg Val Ala
245 250 255

Asp Arg Phe Glu Val Tyr Phe Lys Gly Ile Glu Leu Ala Asn Gly Phe
260 265 270

-continued

```
His Glu Leu Asp Asn Pro Ala Glu Gln Leu Ala Arg Phe Lys Ala Asp
275                 280                 285

Asn Ala Lys Arg Leu Glu Met Gly Leu Thr Glu Gln Pro Ile Asp Tyr
290                 295                 300

His Leu Ile Ala Ala Leu Glu Ala Gly Leu Pro Glu Cys Ala Gly Val
305                 310                 315                 320

Ala Leu Gly Ile Asp Arg Leu Ile Met Leu Ala Leu Gly Glu Asp His
325                 330                 335

Ile Asp Lys Val Thr Ala Phe Pro Phe Pro Arg Ala
340                 345


<210> SEQ ID NO 8
<211> LENGTH: 615
<212> TYPE: PRT
<213> ORGANISM: Homo sapiens

<400> SEQUENCE: 8

Val Leu Ser Ser Leu Leu Leu Gly Arg Ala Leu Arg Glu Asp Gly Gly
1               5                   10                  15

Arg Ala Gly Gly Arg Gly Glu Ser Gly Trp Gln Arg Ala Glu Thr Glu
20                  25                  30

Gln Glu Ala Glu Glu Thr Pro Glu Ser Glu Glu Ser Ser Arg Glu Gly
35                  40                  45

Gly Gln Thr Glu Arg Ala Gln Glu Thr Ala Lys Pro Ser His Cys Cys
50                  55                  60

Cys His Gln Pro His His Trp Cys Gly Ser Gly Arg Glu Arg Gly Pro
65                  70                  75                  80

Lys Ser Ile Leu Gln Asn Pro Gln Ser Ser Asn Ser Ser Ala Glu Gly
85                  90                  95

Gln Trp Gly Arg Pro Ile Pro Thr Gln Val Pro Cys Arg His Leu Thr
100                 105                 110

His Leu His Pro Lys Ile Ser Pro Ala Ala Trp Gly Ser Pro Asp His
115                 120                 125

His Leu Lys Gly Gly Arg Asp Pro Cys Gln Lys Ser Phe Trp Gly Lys
130                 135                 140

Ala His Leu Leu Ser Ser Arg Arg Gly Gly Glu Val Ala Ser His Gly
145                 150                 155                 160

Gln Phe Gln Lys Leu Ile Arg Arg Arg Ile Tyr Ser Tyr Gln Thr Ala
165                 170                 175

Ser Gly Arg His Asn Trp Ser Ser Gly Glu Ser Trp Asn Gln Glu Gly
180                 185                 190

Ala Glu His His Ser Val Asp His Thr Ala Val Ser Leu Phe Ala Tyr
195                 200                 205

Val Thr Ser Ser Ser Leu Trp Ala Gln Arg Gln Gly Asn Lys Val Ser
210                 215                 220

Pro Glu Ile Leu Gly Leu Asp Pro Glu Leu Cys Glu Ala Glu Ile Tyr
225                 230                 235                 240

His Pro Leu Asp His His Ile Tyr Lys Lys Phe Leu Arg Ala Gly Ile
245                 250                 255

Pro Arg Asp Asn Ser His Asp Glu His His Pro Arg Gly Ser Arg Gly
260                 265                 270

Gln Ala Phe His His Leu Ser Gln Arg Ala Gly His Glu Leu Ile Tyr
275                 280                 285

Glu Asn Cys Ser Arg Thr Leu Ser Asp Ala Cys Gly Trp Trp His Arg
290                 295                 300
```

-continued

```
Pro Gly Leu Asn Trp Thr Pro Val Pro Glu Gly Asp Phe Asp Ala Gln
305                 310                 315                 320

Ser Val His His Leu Val Leu His Gly Leu Cys Arg Leu Ser Arg Ser
325                 330                 335

His Gly Asn His Gly Glu Asp Gly Phe Arg Asp Gly Glu Ala Tyr Tyr
340                 345                 350

Arg Gln Leu Gln Gly His Leu Pro Pro Arg Trp Pro Arg Gly Pro Ser
355                 360                 365

Leu Arg Cys Leu His Pro Thr Leu Pro Ala Asn Gln His Gly Arg Arg
370                 375                 380

Ala Glu Ser Pro Gly Asp Glu Ala Ala Arg Asn Glu Pro Leu Asn Arg
385                 390                 395                 400

Asn Ser Gln Asn Ser Tyr Leu Cys Gly Lys Ser Cys Met Pro Ser Thr
405                 410                 415

Ser Asp His Ser Gln Ala Pro Gln Ala Cys Trp Gly Val Pro Gly Ser
420                 425                 430

Asp Leu His Gln Ser Tyr Ile His Leu Ser Pro Thr Asp Asn Glu Pro
435                 440                 445

Phe Gly Met Ala Pro Leu Arg Gly Ser Asp Ala Leu Ala Val Cys His
450                 455                 460

Glu Glu Arg Asp Met Gln Cys Val Tyr Ala Glu Ser His Ala Ala Ala
465                 470                 475                 480

Ala Ala Phe Arg Thr Gly Gln Gly Gln Gly Cys Arg Gly His Val His
485                 490                 495

Arg Lys Leu Leu Tyr Cys Pro Gly Ile Trp Ala Ala Pro His Ser Trp
500                 505                 510

Leu Gly His Gly His Ser Ser Arg His Val Ser His Gly Leu Gln Gln
515                 520                 525

His Gln Gly Ser Thr Ser Val Ser Cys His Glu Thr Arg Arg Gln Glu
530                 535                 540

Gly Glu Cys Ser Asn His Tyr Thr Gly Lys His Asn Ser Trp His Phe
545                 550                 555                 560

Cys Leu Glu Asn Asn Asn Cys Lys Leu Tyr Asn Ser Gly Val Phe Ala
565                 570                 575

Phe Leu Arg Lys Ile Lys Val Cys Lys Gly Ile Leu Val Cys Cys Phe
580                 585                 590

Pro Phe Asp Thr Ala Val Leu Phe Ser His Gln Lys Arg Asp Lys Glu
595                 600                 605

Leu Lys Ile Ser Phe Ser Cys
610                 615


<210> SEQ ID NO 9
<211> LENGTH: 17
<212> TYPE: RNA
<213> ORGANISM: Escherichia coli
<220> FEATURE:
<221> NAME/KEY: modified_base
<222> LOCATION: (8)
<223> OTHER INFORMATION: 5-(N-trifiluoroacetyl)methylaminomethy
      2-thiouridine
<220> FEATURE:
<221> NAME/KEY: modified_base
<222> LOCATION: (11)
<223> OTHER INFORMATION: N6-(N-threonylcarbonyl)adenosine
<220> FEATURE:
<221> NAME/KEY: modified_base
<222> LOCATION: (13)
<223> OTHER INFORMATION: pseudouridine
```

-continued

<400> SEQUENCE: 9
guugacunuu nancaau 17

<210> SEQ ID NO 10
<211> LENGTH: 17
<212> TYPE: RNA
<213> ORGANISM: Salmonella enterica
<220> FEATURE:
<221> NAME/KEY: modified_base
<222> LOCATION: (8)
<223> OTHER INFORMATION: 5-(N-trifiluoroacetyl)methylaminomethy
2-thiouridine
<220> FEATURE:
<221> NAME/KEY: modified_base
<222> LOCATION: (11)
<223> OTHER INFORMATION: N6-(N-threonylcarbonyl)adenosine
<220> FEATURE:
<221> NAME/KEY: modified_base
<222> LOCATION: (13)
<223> OTHER INFORMATION: pseudouridine

<400> SEQUENCE: 10
guugacunuu nancaau 17

<210> SEQ ID NO 11
<211> LENGTH: 17
<212> TYPE: RNA
<213> ORGANISM: Shigella flexneri
<220> FEATURE:
<221> NAME/KEY: modified_base
<222> LOCATION: (8)
<223> OTHER INFORMATION: 5-(N-trifiluoroacetyl)methylaminomethy
2-thiouridine
<220> FEATURE:
<221> NAME/KEY: modified_base
<222> LOCATION: (11)
<223> OTHER INFORMATION: N6-(N-threonylcarbonyl)adenosine
<220> FEATURE:
<221> NAME/KEY: modified_base
<222> LOCATION: (13)
<223> OTHER INFORMATION: pseudouridine

<400> SEQUENCE: 11
guugacunuu nancaau 17

<210> SEQ ID NO 12
<211> LENGTH: 17
<212> TYPE: RNA
<213> ORGANISM: Campylobacter jejuni
<220> FEATURE:
<221> NAME/KEY: modified_base
<222> LOCATION: (8)
<223> OTHER INFORMATION: 5-(N-trifiluoroacetyl)methylaminomethy
2-thiouridine or 5-carboxymethylaminomethyl-2-thiouridine
<220> FEATURE:
<221> NAME/KEY: modified_base
<222> LOCATION: (11)
<223> OTHER INFORMATION: N6-(N-threonylcarbonyl)adenosine

<400> SEQUENCE: 12
ucucccunuu naggagg 17

<210> SEQ ID NO 13
<211> LENGTH: 17
<212> TYPE: RNA
<213> ORGANISM: Vibrio cholerae
<220> FEATURE:
<221> NAME/KEY: modified_base
<222> LOCATION: (8)
<223> OTHER INFORMATION: 5-(N-trifiluoroacetyl)methylaminomethy -continued

```
      2-thiouridine or 5-carboxymethylaminomethyl-2-thiouridine
<220> FEATURE:
<221> NAME/KEY: modified_base
<222> LOCATION: (11)
<223> OTHER INFORMATION: N6-(N-threonylcarbonyl)adenosine

<400> SEQUENCE: 13

guuggcunuu naccaau                                                   17


<210> SEQ ID NO 14
<211> LENGTH: 17
<212> TYPE: RNA
<213> ORGANISM: Listeria monocytogenes
<220> FEATURE:
<221> NAME/KEY: modified_base
<222> LOCATION: (8)
<223> OTHER INFORMATION: 5-(N-trifiluoroacetyl)methylaminomethy
      2-thiouridine or 5-carboxymethylaminomethyl-2-thiouridine
<220> FEATURE:
<221> NAME/KEY: modified_base
<222> LOCATION: (11)
<223> OTHER INFORMATION: N6-(N-threonylcarbonyl)adenosine
<220> FEATURE:
<221> NAME/KEY: modified_base
<222> LOCATION: (13)
<223> OTHER INFORMATION: pseudouridine

<400> SEQUENCE: 14

ucugacunuu nancaga                                                   17


<210> SEQ ID NO 15
<211> LENGTH: 17
<212> TYPE: RNA
<213> ORGANISM: Listeria monocytogenes
<220> FEATURE:
<221> NAME/KEY: modified_base
<222> LOCATION: (11)
<223> OTHER INFORMATION: N6-(N-threonylcarbonyl)adenosine
<220> FEATURE:
<221> NAME/KEY: modified_base
<222> LOCATION: (13)
<223> OTHER INFORMATION: pseudouridine

<400> SEQUENCE: 15

gcugacucuu nancagc                                                   17


<210> SEQ ID NO 16
<211> LENGTH: 17
<212> TYPE: RNA
<213> ORGANISM: Yersinia enterocolitica
<220> FEATURE:
<221> NAME/KEY: modified_base
<222> LOCATION: (8)
<223> OTHER INFORMATION: 5-(N-trifiluoroacetyl)methylaminomethy
      2-thiouridine
<220> FEATURE:
<221> NAME/KEY: modified_base
<222> LOCATION: (11)
<223> OTHER INFORMATION: N6-(N-threonylcarbonyl)adenosine
<220> FEATURE:
<221> NAME/KEY: modified_base
<222> LOCATION: (13)
<223> OTHER INFORMATION: pseudouridine

<400> SEQUENCE: 16

cuugacunuu nancaau                                                   17


<210> SEQ ID NO 17
<211> LENGTH: 17
<212> TYPE: RNA
<213> ORGANISM: Yersinia enterocolitica
```

-continued

```
<220> FEATURE:
<221> NAME/KEY: modified_base
<222> LOCATION: (11)
<223> OTHER INFORMATION: N6-(N-threonylcarbonyl)adenosine
<220> FEATURE:
<221> NAME/KEY: modified_base
<222> LOCATION: (13)
<223> OTHER INFORMATION: pseudouridine

<400> SEQUENCE: 17

cuugacucuu nancaau                                                  17


<210> SEQ ID NO 18
<211> LENGTH: 17
<212> TYPE: RNA
<213> ORGANISM: Yersinia enterocolitica

<400> SEQUENCE: 18

ccagacugaa gaucugg                                                  17


<210> SEQ ID NO 19
<211> LENGTH: 17
<212> TYPE: RNA
<213> ORGANISM: Yersinia enterocolitica
<220> FEATURE:
<221> NAME/KEY: modified_base
<222> LOCATION: (6)
<223> OTHER INFORMATION: 2'-O-methylcytidine
<220> FEATURE:
<221> NAME/KEY: modified_base
<222> LOCATION: (8)
<223> OTHER INFORMATION: 2'-O-methylguanosine
<220> FEATURE:
<221> NAME/KEY: modified_base
<222> LOCATION: (14)
<223> OTHER INFORMATION: 5-methylcytidine

<400> SEQUENCE: 19

ccaganunaa gaunugg                                                  17


<210> SEQ ID NO 20
<211> LENGTH: 17
<212> TYPE: RNA
<213> ORGANISM: Yersinia enterocolitica
<220> FEATURE:
<221> NAME/KEY: modified_base
<222> LOCATION: (6)
<223> OTHER INFORMATION: 2'-O-methylcytidine
<220> FEATURE:
<221> NAME/KEY: modified_base
<222> LOCATION: (8)
<223> OTHER INFORMATION: 2'-O-methylguanosine
<220> FEATURE:
<221> NAME/KEY: modified_base
<222> LOCATION: (11)
<223> OTHER INFORMATION: 1-methylguanosine
<220> FEATURE:
<221> NAME/KEY: modified_base
<222> LOCATION: (13)
<223> OTHER INFORMATION: pseudouridine
<220> FEATURE:
<221> NAME/KEY: modified_base
<222> LOCATION: (14)
<223> OTHER INFORMATION: 5-methylcytidine

<400> SEQUENCE: 20

ccaganunaa nannugg                                                  17


<210> SEQ ID NO 21
<211> LENGTH: 17
<212> TYPE: RNA
```

-continued

```
<213> ORGANISM: Yersinia enterocolitica
<220> FEATURE:
<221> NAME/KEY: modified_base
<222> LOCATION: (10)
<223> OTHER INFORMATION: 2'-O-methylguanosine
<220> FEATURE:
<221> NAME/KEY: modified_base
<222> LOCATION: (12)
<223> OTHER INFORMATION: 2'-O-methylcytidine

<400> SEQUENCE: 21

ggucuagaan unagacc                                                    17
```

COMPOSITIONS AND METHODS FOR THE IDENTIFICATION OF INHIBITORS OF PROTEIN SYNTHESIS

This application claims the benefit of U.S. Provisional Application Nos. 60/866,988, filed Nov. 22, 2006 and 60/867,263, filed Nov. 27, 2006, both of which are incorporated herein by reference in their entirety.

FIELD

The invention generally relates to compositions and methods of identification of inhibitors of protein synthesis.

BACKGROUND

The significant progress in the understanding of the molecular basis of human disease in the last few decades has led to a significant increase in the number of potential therapeutic targets. Over the years many drugs have been developed that target various biological processes such as enzymatic reactions and signal receptors. Among these, protein synthesis inhibitors represent a large potential class of molecular targets with importance that spans across many therapeutic areas, such as antibiotics, antivirals, and anticancer treatments.

One class of under utilized therapeutic targets is the ribonucleic acids (RNAs) involved in bacterial protein synthesis. More specifically, the protein synthesis processes that use post-transcriptional modified RNA nucleotides as substrates may be ideal therapeutic targets. Post-transcriptional nucleotide modifications can be as simple as the addition of a methyl group to a standard nucleotide or complex multi-step addition of amino acid like side chains (Soll, D. and RajBhandary, U. L., tRNA: Structure, Biosynthesis, and Function, ASM Press 1995; Grosjean, H. and Benne, R., Modification and Editing of RNA., Washington, DC, ASM Press, 1998). While 1 to 2% of all RNA bases are modified, the nucleotides in the active sites of the ribosome and the transfer RNA (tRNA) that interact with the ribosome are modified at 10-fold the rate of modification outside these active sites. One of the functions of these modifications is to enhance the selectivity and specificity of the RNA:enzyme interactions that occur during transcription and translation. One such class of enzymes that utilize tRNA containing modified nucleotide bases is the amino acyl tRNA synthetases (AaRS) which catalyze the attachment of a specific amino acid to its corresponding tRNA. The specificity of the AaRS to their respective amino acid can be influenced by many features of the tRNA molecule including the modified nucleotide bases. In the case of the Lysine tRNA synthetase (LysRS), the anticodon stem loop (ASL) of the tRNA contains 2 or 3 modified nucleotide bases depending upon the organism.

There is a need for the identification of inhibitors of protein synthesis from RNA molecules having modified nucleotide bases. To this end, there also remains a need for the development of methods for the identification of such inhibitors. Such inhibitors may be useful for the development of, for example, antimicrobial compounds for use in therapeutic applications.

SUMMARY

Compositions and methods are provided for the identification of inhibitors of protein synthesis. In one aspect, methods of identifying an inhibitor of tRNA-target molecule binding, comprise the steps of (1) forming a mixture of a first nucleic acid molecule comprising a tRNA TΨC-loop fragment, a target molecule capable of binding to the tRNA TΨC-loop fragment, and a test compound, where the tRNA TΨC-loop fragment contains at least one modified nucleotide; (2) incubating the mixture under conditions that allow binding of the tRNA TΨC-loop fragment and the target molecule in the absence of the test compound; and (3) detecting whether or not the test compound inhibits the binding of the tRNA TΨC-loop fragment and the target molecule, wherein the absence of binding of the tRNA fragment and the target molecule is indicative of the test compound being an inhibitor of tRNA-target molecule binding.

In another aspect, methods of identifying an inhibitor of tRNA-target molecule interaction, comprise the steps of (1) forming a mixture comprising a first nucleic acid molecule comprising a tRNA D-loop fragment, a target molecule capable of binding to the tRNA D-loop fragment, and a test compound, where the tRNA D-loop fragment contains at least one modified nucleotide; (2) incubating the mixture under conditions that allow binding of the tRNA D-loop fragment and the target molecule in the absence of the test compound; and (3) detecting whether or not the test compound inhibits the binding of the tRNA D-loop fragment and the target molecule, where the absence of binding of the tRNA fragment and the target molecule is indicative of the test compound being an inhibitor of tRNA-target molecule interaction.

In a further aspect, methods of diagnosing whether a subject has a bacterial infection, comprise the steps of (1) forming a mixture comprising a first nucleic acid molecule derived from a fragment of a tRNA molecule comprising at least one modified nucleotide and a biological sample from a subject, where the fragment tRNA molecule corresponds to a TΨC-loop, a D-loop, or an anticodon stem loop structure; (2) incubating the mixture under conditions that allow binding of the first nucleic acid molecule and a target molecule indicative of the presence of a bacteria in the absence of the test compound; and (3) detecting whether the first nucleic acid molecule binds to the target molecule, where the binding of the first nucleic acid molecule and the target molecule is indicative of the positive diagnosis of a bacterial infection in the biological sample.

In another aspect, microarrays are provided comprising a plurality of nucleic acid molecules having at least one modified nucleotide and a solid support to which the plurality of nucleic acid molecules are attached.

In another aspect, isolated nucleic acid molecules are provided comprising a nucleic acid fragment derived from a tRNA D-loop having at least one modified nucleotide. In still another aspect, isolated nucleic acid molecules are provided comprising a nucleic acid fragment derived from a tRNA TΨC-loop having at least one modified nucleotide.

In a further aspect, methods of identifying a target molecule that binds to a RNA molecule are provided comprising the steps of (1) forming a mixture comprising a biological sample and at least one nucleic acid molecule derived from or corresponding to a tRNA loop having at least one modified nucleotide, where the tRNA loop is selected from the group consisting of a TΨC-loop, a D-loop, and an anticodon loop; (2) incubating the mixture under conditions that allow binding of a target molecule in the biological sample to the first nucleic acid molecule; and (3) detecting whether a target molecule binds to the first nucleic acid molecule.

BRIEF DESCRIPTION OF THE DRAWINGS

FIGS. 1 A-D provide an amino acid sequence alignment of the LysRS sequences from food and water borne bacteria species included on the Category B pathogen list compared to human sequence. The LysRS sequence is highly conserved across 3 of the 7 species and has very little homology with the human sequence.

DETAILED DESCRIPTION

Figure 2:
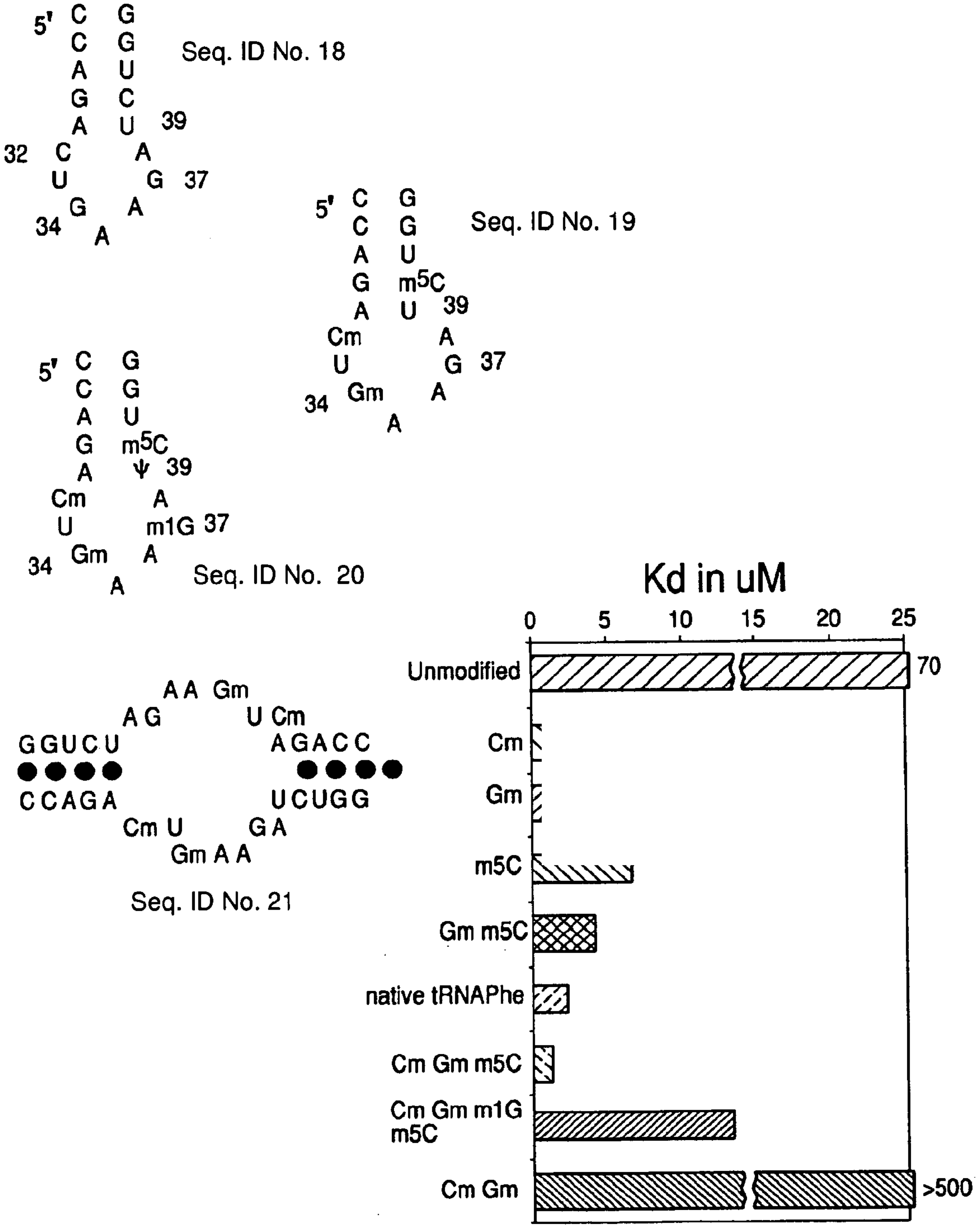
FIG. 2 provides the sequences of RNA oligomers containing various modified nucleotides used in binding experiments using a peptide mimic of phenylalanine synthetase, as well as the results of binding experiments using the phenylalanine synthetase peptide mimic.
Figure 3:
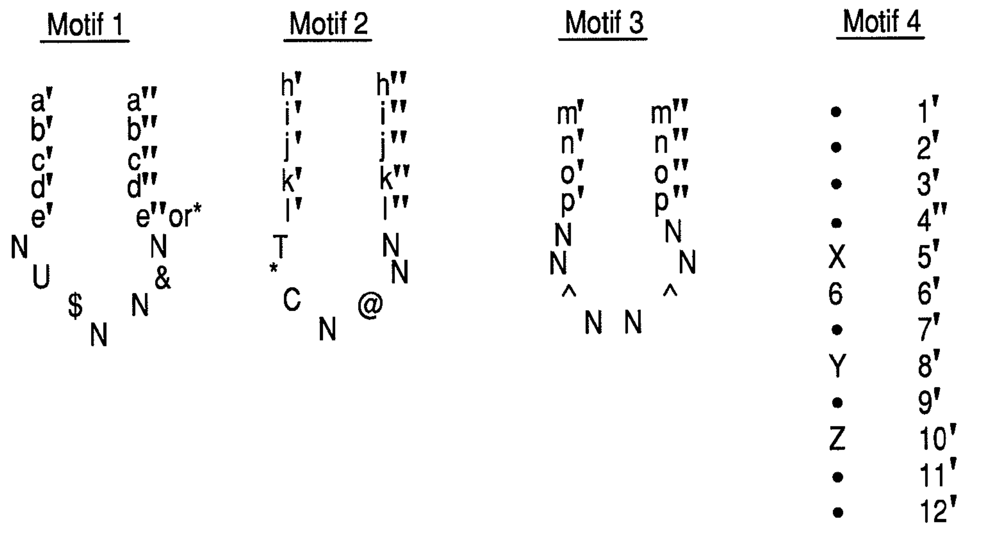
FIG. 3 provides representative sequences for tRNA fragments containing various modified nucleotide bases. Motif 1 represents one embodiment of a tRNA anticodon-stem loop structure containing modified nucleotides. Motif 2 represents one embodiment of a tRNA TΨC loop fragment containing modified nucleotides. Motif 3 represents one embodiment of a tRNA D-loop fragment containing modified nucleotides. Motif 4 represents one embodiment of a linear tRNA-anticodon fragment containing modified nucleotides.
Figure 4:
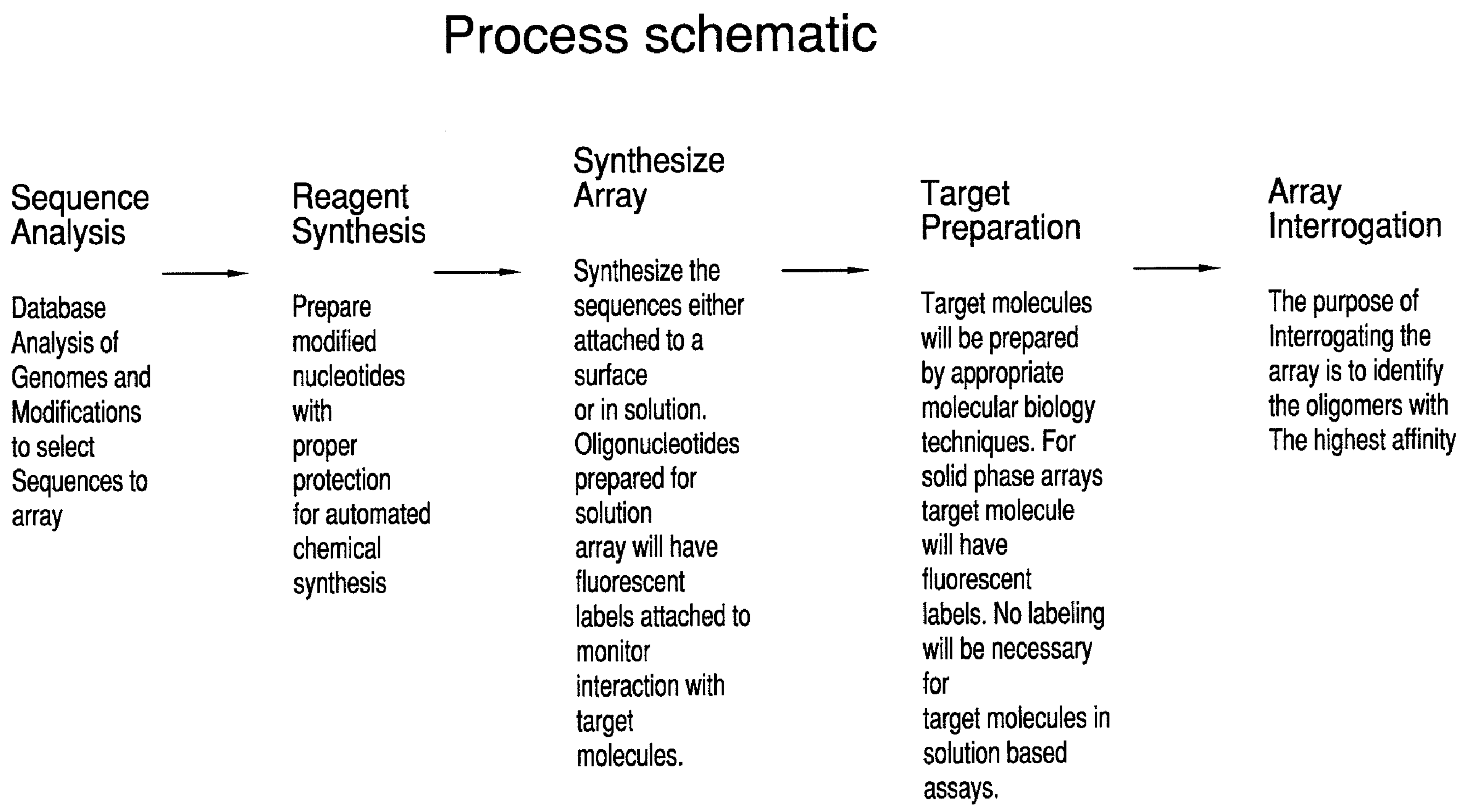
FIG. 4 provides, in one aspect, a schematic of a process for developing an array having nucleic acid molecules containing modified nucleotides and interrogating the array with target molecules.

The present disclosure relates to compositions and methods for the identification of compounds useful for inhibiting protein synthesis. The compositions and methods are useful for the identification of inhibitors of the interactions of RNA having one or more modified nucleotide bases with a target molecule. Thus, the disclosure generally relates to compositions and methods for the identification of inhibitors of RNA-target molecule interactions.

Prior to describing this invention in further detail, however, the following terms will first be defined.

DEFINITIONS

As used herein, an "inhibitor" refers to any compound capable of preventing, reducing, or restricting the interaction or binding of a nucleic acid molecule having at least one modified nucleotide base to a target molecule. An inhibitor may inhibit such interaction or binding, for example, by preventing, reducing or restricting binding of nucleic acid molecule to the binding site of a target molecule. In some embodiments, the inhibition is at least 20% (e.g., at least 50%, 70%, 80%, 90%, 95%, 98%, 99%, 99.5%) of the binding as compared to the binding in the absence of the inhibitor. In one aspect, an inhibitor prevents, reduces, or restricts the binding of a transfer RNA (tRNA), or fragment thereof, to a target molecule. Assays for analyzing inhibition are described herein.

As used herein, a "label" or "detectable label" is any composition that is detectable, either directly or indirectly for example, by spectroscopic, photochemical, biochemical, immunochemical, or chemical means). Useful labels include, but are not limited to, radioactive isotopes (for example, $^{32}P$, $^{35}S$, and $^{3}H$), dyes, fluorescent dyes (for example, Cy5 and Cy3), fluorophores (for example, fluorescein), electron-dense reagents, enzymes and their substrates (for example, as commonly used in enzyme-linked immunoassays, such as, alkaline phosphatase and horse radish peroxidase), biotin-streptavidin, digoxigenin, or hapten; and proteins for which antisera or monoclonal antibodies are available. Moreover, a label or detectable moiety can include an "affinity tag" that, when coupled with the target molecule and incubated with a test compound or compound library, allows for the affinity capture of the target molecule along with molecules bound to the target molecule. One skilled in the art will appreciate that an affinity tag bound to the target molecule has, by definition, a complimentary ligand coupled to a solid support that allows for its capture. For example, useful affinity tags and complimentary partners include, but are not limited to, biotin-streptavidin, complimentary nucleic acid fragments (for example, oligo dT-oligo dA, oligo T-oligo A, oligo dG-oligo dC, oligo G-oligo C), aptamers, or haptens and proteins for which antisera or monoclonal antibodies are available. The label or detectable moiety is typically bound, either covalently, through a linker or chemical bound, or through ionic, van der Waals or hydrogen bonds to the molecule to be detected.

As used herein, a "modified nucleotide" refers to any modification of a nucleotide base. Modified nucleotide bases include, but are not limited to, but not limited to, unknown modified adenosine (?A); 1-methyladenosine (m1A); 2-methyladenosine (m2A); $N^6$-isopentenyladenosine (i6A); 2-methylthio-$N^6$-isopentenyladenosine (ms2i6A); $N^6$-methyladenosine (m6A); $N^6$-threonylcarbamoyladenosine (t6A); $N^6$-methyl-$N^6$-threonylcarbomoyladenosine (m6t6A); 2-methylthio-$N^6$-threonylcarbamoyladenosine (ms2t6A); 2'-O-methyladenosine (Am); I Inosine (I); 1-methylinosine Ar(m1I); 2'-O-(5-phospho)ribosyladenosine (Ar(p)); $N^6$-(cis-hydroxyisopentenyl)adenosine (io6A); Unknown modified cytidine (?C); 2-thiocytidine (s2C); 2'-O-methylcytidine (Cm); $N^4$-acetylcytidine (ac4C); 5-methylcytidine (m5C); 3-methylcytidine (m3C); lysidine (k2C); 5-formylcytidin (f5C); 2'-O-methyl-5-formylcytidin (f5Cm); unknown modified guanosine (?G); 2'-O-(5-phospho)ribosylguanosine (Gr (p)); 1-methylguanosine (m1G); $N^2$-methylguanosine (m2G); 2'-O-methylguanosine (Gm); $N^2N^2$-dimethylguanosine (m22G); $N^2$,$N^2$,2'-O-trimethylguanosine (m22Gm); 7-methylguanosine (m7G); archaeosine (fa7d7G); queuosine (Q); mannosyl-queuosine (manQ); galactosyl-queuosine (galQ); wybutosine (yW); peroxywybutosine (o2yW); unknown modified uridine (?U); 5-methylaminomethyluridine (mnm5U); 2-thiouridine (s2U); 2'-O-methyluridine (Um); 4-thiouridine (s4U); 5-carbamoylmethyluridine (ncm5U); 5-methoxycarbonylmethyluridine (mcm5U); 5-methylaminomethyl-2-thiouridine (mnm5s2U); 5-methoxycarbonylmethyl-2-thiouridine (mcm5s2U); uridine 5-oxyacetic acid (cmo5U); 5-methoxyuridine (mo5U); 5-carboxymethylaminomethyluridine (cmnm5U); 5-carboxymethylaminomethyl-2-thiouridine (cmnm5s2U); 3-(3-amino-3-carboxypropyl)uridine (acp3U); 5-(carboxyhydroxymethyl)uridinemethyl ester (mchm5U); 5-carboxymethylaminomethyl-2'-O-methyluridine (cmnm5Um); 5-carbamoylmethyl-2'-O-methyluridine (ncm5Um); Dihydrouridine (D); pseudouridine (Ψ); 1-methylpseudouridine (m1Ψ); 2'-O-methylpseudouridine (Ψm); ribosylthymine (m5U); 5-methyl-2-thiouridine (m5s2U); and 5,2'-O-dimethyluridine (m5Um).

As used herein, a "target molecule" refers to any biological molecule of interest or molecule that is capable of binding to a nucleic acid molecule having at least one modified nucleotide under physiological conditions. The biological molecule of interest can be any class of biological molecule, including, but not limited to, ligands, receptors, peptides, proteins, enzymes, polypeptides, nucleic acids (oligonucleotide or polynucleotide of RNA or DNA), antibodies, epitopes, hormones, oligosaccharides, or any other biological molecules. In one aspect, target protein molecules include proteins involved in protein synthesis, including proteins involved in RNA maturation and proteins involved in translation. Particular target molecules include any molecule involved in protein synthesis, such as, for example, aminoacyl tRNA synthetases, methyl transferases, pseudouridine synthases, ribosomes, retroviral reverse transcriptases, messenger RNAs, tRNA, viral RNA or fragments thereof. For example, if transcripts of genes are the interest of an experiment, the target molecules would include mRNA. Other examples include protein fragments, small molecules, etc. “Target nucleic acid” refers to a nucleic acid (often derived from a biological sample) of interest that is capable of binding, or otherwise interacting with, an RNA molecule. Target nucleic acid molecules include RNA and DNA molecules involved in binding to tRNA loop sequences having at least one modified nucleotide. A target molecule may be detected using one or more nucleic acid molecules having at least one modified nucleotide.

Methods are provided for identifying inhibitors of RNA binding to a target molecule. The methods generally involve forming a mixture of a RNA molecule having at least one modified nucleotide, a target molecule capable of binding to the RNA molecule and a test compound, and incubating the mixture under conditions that allow the binding of the RNA molecule and the target molecule in the absence of the test molecule.

The nucleic acid molecules may be derived from any ribonucleic acid, such as messenger RNA (mRNA), transfer RNA (tRNA), mitochondrial RNA (mtRNA), ribosomal RNA (rRNA), and nuclear RNA (nRNA). In another aspect, the ribonucleic acid molecules may comprise fragments of any such ribonucleic acids. For example, tRNA generally contains four stem loop structures: the TΨC-loop, the D-loop, a variable loop and the anticodon stem-loop. In addition to the four stem loop structures, the tRNA contains an acceptor arm for attachment of a particular amino acid for incorporation into a peptide chain. The nucleic acid molecule for use in the methods disclosed herein may comprise any one of the loop structures of a tRNA. For example, a tRNA TΨC-loop fragment refers to a nucleic acid sequence derived from, or corresponding to, the TΨC-loop sequence of a tRNA and includes at least part of the antiparallel stem structure of the loop. In addition, the RNA molecule may consist essentially of one of the loop structures and include additional nucleic acid sequences not derived from, or not corresponding to, the same native RNA molecule and may include detectable labels for use in the methods. The RNA molecule may also consist essentially of one of the loop structures in addition to one additional loop structure derived from, or corresponding to, the same native RNA molecule, and may contain additional nucleotides or labels. For example, the ribonucleic acid sequence may comprise an anticodon stem-loop sequence, a TΨC-loop sequence, or a D-loop sequence. A ribonucleic acid molecule may also comprise a TΨC-loop sequence in combination with an anticodon stem loop sequence. In addition, the molecule may further comprise the acceptor arm of the tRNA molecule.

The nucleic acid molecules may contain any number of modified or unmodified nucleotides. In one aspect, the ribonucleic acid molecules incorporate one, two, three, or more modified nucleotides into the nucleic acid sequence. Where two or more modified nucleotides are incorporated into a nucleic acid molecule, the modified nucleotides may be the same or may be different modified nucleotides. In another aspect, the nucleic acid molecules incorporate three or more modified nucleotides into the nucleic acid molecule.

The nucleic acid molecules containing the modified nucleotides may be linear or may form secondary or tertiary structures, such as loop structures, bulges, pseudoknots, or turns. Nucleic acid molecules may form secondary or tertiary structures for any reason, such as, for example, stem-loop structures by the inclusion of complementary nucleotides at the 5' and 3' terminal ends of the molecule. Nucleic acid molecules having secondary or tertiary structures may be employed in the methods discloses herein depending on the target molecule to which the nucleic acid molecule interacts.

The ribonucleic acid molecules may have any number of nucleotides, such as, for example, 10, 11, 12, 13, 14, 15, 16, 17, 18, 19, 20, 25, 30, 35, 40, 45, 50, 100, or more nucleotides. In one aspect, the ribonucleic acid molecule is derived from a nucleic acid sequence of a tRNA. Where the nucleic acid molecule is derived from a tRNA, the tRNA may contain modified nucleotides within the sequence corresponding to one or more of the loop structures, such as the TΨC-loop, the D-loop, or the anticodon stem loop (ASL). In one aspect, the modifications may correspond to positions 34, 37, and 39 in the anticodon stem loop of a tRNA. In another aspect, the modified nucleotides may correspond to positions 53, 54, and 57 in the TΨC-loop of a tRNA. In a further aspect, the modifications may correspond to positions 16 and 19 in the D-loop of a tRNA. In another aspect, the modifications may correspond to combinations of any of these positions in the anticodon stem loop, the TΨC-loop, or the D-loop. The position numbers used herein refer to the nucleotide position numbering of the conventional tRNA numbering as disclosed in Sprinzl, et al. *Nucl. Acids. Res.,* 26, 148-153 (1998).

A tRNA fragment may comprise a nucleic acid molecule derived from or corresponding to an anticodon stem loop (ASL) of a tRNA molecule. In one aspect, a tRNA fragment derived from or corresponding to an ASL comprises the nucleic acid sequence:

5'-a'b'c'd'e'NUXNNYNe"(or Z)d"c"b"a";

where X, Y, and Z refer to modified nucleotides, a', b', c', d', e', a", b", c", d", and e" refer to any nucleotide and a', b', c', d', and e' are complementary to a", b", c", d", and e", respectively, and N refers to any nucleotide.

In one aspect, X refers to mnm5s2U, s2U, mnm5U, and mcm5s2U;

Y refers to t6A, m2A, and ms2t6A, and

Z refers to ψ.

In another aspect, the tRNA fragment comprises a nucleic acid molecule derived from or corresponding to the TΨC-loop of a tRNA molecule. In one aspect, a tRNA fragment derived from or corresponding to TΨC-loop comprises the nucleic acid sequence 5'-h'i'j'k'l'(ribothymidine)(Psi)CN(m1A)NNl"k"j"i"h", where h', i', j', k', l', h", i", j", k", and l" refer to any nucleotide and h', i', j', k', and l' are complementary to h", i", j", k", and l", respectively, and N refers to any nucleotide.

In another aspect, the tRNA fragment may comprise a nucleic acid molecule derived from or corresponding to the D-loop of a tRNA molecule. In one aspect, a tRNA fragment derived from or corresponding to a D-loop comprises the nucleic acid sequence 5'-m'n'o'p'NN(dihydrouridine)NN(dihydrouridine) NNp"o"n"m", where m', n', o', p', m", n", o", and p" are any nucleotide and m', n', o', and p' are complementary to m", n", o", and p", respectively, and N refers to any nucleotide.

In another aspect, the tRNA fragment comprises a nucleic acid molecule derived from or corresponding to the ASL of a tRNA molecule. In one aspect, a tRNA fragment derived from or corresponding to the ASL comprises the nucleic acid sequence 5'-$N^1N^2N^3N^4$(mcm5s2U)$N^6N^7$(ms2t6A)$N^9$(pseudouridine)$N^{11}N^{12}$, where $N^1$, $N^2$, $N^3$, $N^4$, $N^6$, $N^7$, $N^9$, $N^{11}$, and $N^{12}$ refer to any nucleotide.

Such ASL fragments may be linear fragments.

The tRNA fragments (or "probe tRNA fragments") for use in the methods of the present disclosure can be a fragment derived from any tRNA. The tRNA fragment may be obtained or derived from or corresponds to a $tRNA^{Ala}$, $tRNA^{Arg}$, $tRNA^{Asn}$, $tRNA^{Asp}$, $tRNA^{Cys}$, $tRNA^{Gln}$, $tRNA^{Glu}$, $tRNA^{Gly}$, $tRNA^{His}$, $tRNA^{Ile}$, $tRNA^{Leu}$, $tRNA^{Lys}$, $tRNA^{Met}$, $tRNA^{Phe}$, $tRNA^{Pro}$, $tRNA^{Ser}$, $tRNA^{Thr}$, $tRNA^{Trp}$, $tRNA^{Tyr}$, or $tRNA^{Val}$. In one aspect, the tRNA fragment corresponds to $tRNA^{Lys}$. In another aspect, the tRNA fragment is derived from or corresponds to the $tRNA^{Lys}$ anticodon stem loop (ASL). In another aspect, the tRNA fragment corresponds to a fragment consisting of nucleotides 32-43 of a bacterial $tRNA^{Lys}$. In a further aspect, the tRNA fragment corresponds to a fragment consisting of nucleotides 32-43 of the human $tRNA^{Lys}$. The position numbers used herein refer to the nucleotide position numbering of the conventional tRNA numbering as disclosed in Sprinzl, et al. *Nucl. Acids. Res.,* 26, 148-153 (1998). In one aspect, the tRNA fragment is a fragment from a host cell tRNA, such as a mammalian host cell, including, but not limited to, human, feline, and simian host cells.

The tRNA fragment may correspond to any portion of the tRNA involved in interacting, directly or indirectly, to the target molecule. In one aspect, the tRNA fragment corresponds to the TΨC-loop, the D-loop or the anticodon stem loop (ASL) of the tRNA, or combinations thereof.

The tRNA fragment may correspond to any portion of the host cell's tRNA involved in nucleotide binding, such as the portion of the tRNA involved in the reverse transcription (RT) complex formation. For example, the tRNA may be involved in binding to a retroviral genome to initiate, prime, or facilitate reverse transcription of the retroviral genome. In one aspect, the fragment tRNA corresponds to a fragment of the anticodon stem loop of any tRNA. In one aspect, the fragment corresponds to a fragment from the anticodon stem loop of tRNA-Lys. In another aspect, the tRNA fragment corresponds to a fragment from the anticodon stem loop of human tRNA-Lys. In another aspect, the tRNA fragment corresponds to a fragment from nucleotides 32-43 of human tRNA-Lys3.

In another aspect, the tRNA fragments correspond to a portion of a bacterial host cell tRNA involved in protein synthesis in the bacterial host cell. For example, the tRNA fragment may be derived from a TΨC-loop, the D-loop or ASL from a bacterial tRNA that binds to bacterial molecules involved in protein synthesis. Bacterial molecules involved in protein synthesis include, but are not limited to aminoacyl tRNA synthetases, methyl transferases, pseudouridine synthases, tRNA sulfurtransferase, tRNA thiolase (ThiI), tRNA-guanine transglycosylase, ribosomal RNA (e.g. 5S ribosomal RNA), and transfer RNA. Each of the TΨC-loop, the D-loop or ASL may be involved in the binding of such molecules and may be important or required for protein synthesis in a bacterial host. In one aspect, test compounds that inhibit the binding of the bacterial tRNA to molecules involved in protein synthesis do not inhibit the binding a mammalian tRNAs to molecules involved in mammalian protein synthesis.

The tRNA fragment may also be any length of a fragment from a tRNA. In one aspect, the tRNA fragment comprises a fragment of between 5 to 25 continuous nucleotides of a tRNA, 7 to 20 continuous nucleotides of a tRNA, or between 10 to 20 continuous nucleotides of a tRNA. In another aspect, the fragment is a fragment of 8, 9, 10, 11, 12, 13, 14, 15, 16, 17, 18 continuous nucleotides of a tRNA. In a further aspect, the fragment is a fragment of 12 continuous nucleotides of a tRNA ASL.

In some aspects, the tRNA ASL fragment may or may not be capable of forming a secondary structure. In a one aspect, the tRNA ASL fragment is not capable of forming a stem loop structure with itself. In another aspect, the fragment is a linear fragment of a tRNA that is not capable of forming a stem loop structure with itself.

The tRNA fragment may also be linked to additional nucleic acids. For example, a tRNA fragment may be linked to one or more additional nucleic acids depending on the assay method. In one aspect, the tRNA fragment may be linked to nucleotides used to attach the fragment to a solid support surface. In another aspect, the fragment tRNA is linked to additional nucleic acid molecules at one or both terminal ends of the tRNA fragment. In another aspect, the fragment tRNA is linked to additional nucleic acid molecules at both terminal ends. The additional nucleic acid sequences can be any length, preferably between 8 and 16 nucleotides, between 10 and 14 nucleotides, more preferably 12 nucleotides in length. In one aspect, the terminal sequences do not allow the tRNA fragment to form a secondary structure, such as a loop structure.

A variety of methods are known in the art for making nucleic acids having a particular sequence or that contain particular nucleic acid bases, sugars, internucleotide linkages, chemical moieties, and other compositions and characteristics. Any one or any combination of these methods can be used to make a nucleic acid, polynucleotide, or oligonucleotide for the present invention. Said methods include, but are not limited to: (1) chemical synthesis (usually, but not always, using a nucleic acid synthesizer instrument); (2) post-synthesis chemical modification or derivatization; (3) cloning of a naturally occurring or synthetic nucleic acid in a nucleic acid cloning vector (e.g., see Sambrook, et al., Molecular Cloning: A Laboratory Approach $2^{nd}$ ed., Cold Spring Harbor Laboratory Press, 1989) such as, but not limited to a plasmid, bacteriophage (e.g., m13 or lamda), phagemid, cosmid, fosmid, YAC, or BAC cloning vector, including vectors for producing single-stranded DNA; (4) primer extension using an enzyme with DNA template-dependent DNA polymerase activity, such as, but not limited to, Klenow, T4, T7, rBst, Taq, Tfl, or Tth DNA polymerases, including mutated, truncated (e.g., exo-minus), or chemically-modified forms of such enzymes; (5) PCR (e.g., see Dieffenbach, C. W., and Dveksler, eds., PCR Primer: A Laboratory Manual, 1995, Cold Spring Harbor Laboratory Press, Cold Spring Harbor, N.Y.); (6) reverse transcription (including both isothermal synthesis and RT-PCR) using an enzyme with reverse transcriptase activity, such as, but not limited to, reverse transcriptases derived from avian myeloblasosis virus (AMV), Maloney murine leukemia virus (MMLV), *Bacillus stearothermophilus* (rBst), *Thermus thermophilus* (Tth); (7) in vitro transcription using an enzyme with RNA polymerase activity, such as, but not limited to, SP6, T3, or T7 RNA polymerase, Tth RNA polymerase, *E. coli* RNA polymerase, or another enzyme; (8) use of restriction enzymes and/or modifying enzymes, including, but not limited to exo- or endonucleases, kinases, ligases, phosphatases, methylases, glycosylases, terminal transferases, including kits containing such modifying enzymes and other reagents for making particular modifications in nucleic acids; (9) use of polynucleotide phosphorylases to make new randomized nucleic acids; (10) other compositions, such as, but not limited to, a ribozyme ligase to join RNA molecules; and/or (11) any combination of any of the above or other techniques known in the art. Oligonucleotides and polynucleotides, including chimeric (i.e., composite) molecules and oligonucleotides with non-naturally-occurring bases, sugars, and internucleotide linkages are commercially available (e.g., see the 2000 Product and Service Catalog, TriLink Biotechnologies, San Diego, Calif., USA)

The RNA molecule or the target molecule, or both the RNA molecule and the target molecule may be labeled to facilitate detection. In one aspect, the RNA molecule is labeled with a fluorophore to facilitate detection. In another aspect, the target molecule is labeled with biotin to facilitate detection. In yet another aspect, the RNA molecule is labeled with a fluorophore and the target molecule is labeled with biotin.

In another aspect, the ribonucleic acid molecules having one or more modified nucleic acids may be immobilized on a substrate to create an array. An "array" may comprise a solid support with nucleic acid probes attached to the support. Arrays may comprise a plurality of different nucleic acids that are coupled to a surface of a substrate in different, known locations. These arrays, also described as "microarrays" or colloquially "chips" have been generally described in the art, for example, in Fodor et al., Science, 251:767-777 (1991). Methods of forming high density arrays of oligonucleotides, peptides and other polymer sequences with a minimal number of synthetic steps are disclosed in, for example, U.S. Pat. Nos. 5,143,854, 5,252,743, 5,384,261, 5,405,783, 5,424,186, 5,429,807, 5,445,943, 5,510,270, 5,677,195, 5,571,639, and 6,040,138. The oligonucleotide analogue array can be synthesized on a solid substrate by a variety of methods, including, but not limited to, light-directed chemical coupling, and mechanically directed coupling. See Pirrung et al., U.S. Pat. No. 5,143,854 (see also PCT Application No. WO 90/15070) and Fodor et al., PCT Publication Nos. WO 92/10092 and WO 93/09668, U.S. Pat. Nos. 5,677,195, 5,800,992 and 6,156,501 which disclose methods of forming vast arrays of peptides, oligonucleotides and other molecules using, for example, light-directed synthesis techniques. See also, Fodor et al., Science, 251, 767-77 (1991). These procedures for synthesis of polymer arrays are now referred to as VLSIPS® procedures. Using the VLSIPS® approach, one heterogeneous array of polymers is converted, through simultaneous coupling at a number of reaction sites, into a different heterogeneous array. See, U.S. Pat. Nos. 5,384,261 and 5,677,195.

Methods for making and using molecular probe arrays (particularly nucleic acid probe arrays) are also disclosed in, for example, U.S. Pat. Nos. 5,143,854, 5,242,974, 5,252,743, 5,324,633, 5,384,261, 5,405,783, 5,409,810, 5,412,087, 5,424,186, 5,429,807, 5,445,934, 5,451,683, 5,482,867, 5,489,678, 5,491,074, 5,510,270, 5,527,681, 5,527,681, 5,541,061, 5,550,215, 5,554,501, 5,556,752, 5,556,961, 5,571,639, 5,583,211, 5,593,839, 5,599,695, 5,607,832, 5,624,711, 5,677,195, 5,744,101, 5,744,305, 5,753,788, 5,770,456, 5,770,722, 5,831,070, 5,856,101, 5,885,837, 5,889,165, 5,919,523, 5,922,591, 5,925,517, 5,658,734, 6,022,963, 6,150,147, 6,147,205, 6,153,743, 6,140,044 and D430024. In one aspect, the ribonucleic acid molecule is a labeled with a detectable label, such as a fluorescent label. A sample containing a target molecule is contacted with the array under appropriate conditions. The arrays are washed or otherwise processed to remove non-bound molecules. The reaction is then evaluated by detecting the distribution of the label on the chip. The distribution of label may be detected by scanning the arrays to determine florescence intensities distribution. Methods for signal detection and processing of intensity data are disclosed in, for example, U.S. Pat. Nos. 5,547,839, 5,578,832, 5,631,734, 5,800,992, 5,856,092, 5,936,324, 5,981,956, 6,025,601, 6,090,555, 6,141,096, 6,141,096, and 5,902,723. Methods for array based assays, computer software for data analysis and applications are disclosed in, for example, U.S. Pat. Nos. 5,527,670, 5,527,676, 5,545,531, 5,622,829, 5,631,128, 5,639,423, 5,646,039, 5,650,268, 5,654,155, 5,674,742, 5,710,000, 5,733,729, 5,795,716, 5,814,450, 5,821,328, 5,824,477, 5,834,252, 5,834,758, 5,837,832, 5,843,655, 5,856,086, 5,856,104, 5,856,174, 5,858,659, 5,861,242, 5,869,244, 5,871,928, 5,874,219, 5,902,723, 5,925,525, 5,928,905, 5,935,793, 5,945,334, 5,959,098, 5,968,730, 5,968,740, 5,974,164, 5,981,174, 5,981,185, 5,985,651, 6,013,440, 6,013,449, 6,020,135, 6,027,880, 6,027,894, 6,033,850, 6,033,860, 6,037,124, 6,040,138, 6,040,193, 6,043,080, 6,045,996, 6,050,719, 6,066,454, 6,083,697, 6,114,116, 6,114,122, 6,121,048, 6,124,102, 6,130,046, 6,132,580, 6,132,996 and 6,136,269.

The use of high-density arrays allows for the development of high throughput assays for the disclosed methods. Such high throughput (HTS) assays may involve attaching or binding either the ribonucleic acid molecule or the target molecule to a solid support. A "solid support" may be any surface to which molecules may be attached through either covalent or non-covalent bonds. This includes, but is not limited to, membranes, plastics, magnetic beads, charged paper, nylon, Langmuir-Bodgett films, functionalized glass, germanium, silicon, PTFE, polystyrene, gallium arsenide, gold, and silver. Any other material known in the art that is capable of having functional groups such as amino, carboxyl, thiol or hydroxyl incorporated on its surface, is also contemplated. This includes surfaces with any topology, including, but not limited to, spherical surfaces and grooved surfaces. HTS methods generally refer to technologies that permit the rapid assaying of test compounds for therapeutic potential, for example, by inhibiting the binding of a tRNA fragment to a target nucleic acid molecule. HTS techniques may employ robotic handling of test materials, detection of positive signals, and interpretation of data. Test compounds may be identified via the detection of luminescence or absence of luminescence through the use of radioactivity or through optical assays that rely on absorbence, fluorescence or luminescence as read-outs. Gonzalez, J. E. et al., (1998) *Curr. Opin. Biotech.* 9:624-631.

Such microarrays containing the ribonucleic acid molecules of the present disclosure may be used in combination with any of the methods disclosed herein for the development of high-throughput assays. Nucleic acid molecules for use in developing such microarrays may be identified by first analyzing databases of various genomes and nucleotide modifications to select desired sequences. Modified nucleotides are then prepared using proper protection for automated chemical synthesis. Nucleic acid molecules are synthesized incorporating the modified nucleotides. The nucleic acid molecules are synthesized either attached to a solid support surface or in solution. Oligonucleotides prepared for solution array will have fluorescent labels attached to monitor interaction or binding with target molecules. Target molecules are prepared by appropriate methods. For solid phase arrays, the target molecule will have fluorescent labels attached, while no labeling is needed for solution based assays. The arrays are then interrogated with the target molecule solutions to identify nucleic acid molecules having the highest affinity for the target molecules.

The ribonucleic acid molecules may be used in methods of identifying an inhibitor of nucleic acid-target molecule interactions. The methods can be used to identify any inhibitor of such interactions. In one aspect, the method can be used to identify inhibitors of RNA-target molecule binding. In one aspect, the methods can be used to identify inhibitors of protein synthesis. In another aspect, the methods can be used to identify inhibitors of tRNA binding to a target nucleic acid molecule. In another aspect, the methods can be used to identify inhibitors of tRNA binding to a target aminoacyl RNA synthetase. In a further aspect, the methods can be used to identify inhibitors of tRNA binding to a target ribosome. In another aspect, the methods can be used to identify inhibitors of tRNA modification enzymes. In another aspect, the methods can be used to identify inhibitors of tRNA binding to a target viral reverse transcriptase.

In another aspect, the methods can be readily adapted for use in high-throughput assays using high-density arrays having one or more RNA probe molecules attached. Transfer RNA (tRNA) is capable of interacting with numerous biological molecules such as those involved in protein synthesis, transcription, translation, reverse transcription, and the like. Identifying inhibitors of such interactions may lead to the identification of therapeutic compounds for use in treating diseases or infections in a host cell. In one aspect, the target molecule is essential to protein synthesis. In one aspect, compounds that inhibit the binding of the bacterial tRNA to molecules involved in protein synthesis do not inhibit the binding a mammalian tRNAs to molecules involved in mammalian protein synthesis.

The inhibitors that are identified by the disclosed methods may be useful for treating any infectious disease or condition in a host cell, such as, for example, bacterial diseases, viral diseases, including retroviral diseases, protozoan diseases, and fungal diseases.

Bacterial diseases for which inhibitors can be identified by the methods disclosed herein include any bacterial disease, such as infections caused by, for example, category A, B, or C pathogens. Category A bacteria include, but are not limited to, *Bacillus antracis, Clostidium botulinum, Francisella tularensis*, and *Yersinia pestis*. Category B bacteria include, but are not limited to *Burkholderia pseudomallei Burkjolderia mallei, Clostridium perfringens, Coxiella burnetii, Brucella melitensis, Brucella abortus, Brucella canis, Staphylococcus aureus, Rickettsia prowazekii, Chlamydia psittaci*, and food and water borne bacteria, such as *Escherichia coli* O157:H7.

Viral Diseases for which inhibitors can be identified by any of the methods disclosed herein include, for example, retroviruses (including lentivirus) and other viral diseases, such as viral encephalitis.

Retroviruses for which inhibitors can be identified by the methods disclosed herein include any viruses having RNA as their primary genetic material and use reverse transcription to produce DNA. Such viruses include, but are not limited to, Feline Immunodeficiency Virus (FIV), Simian Immunodeficiency Virus (SIV), Avian Leucosis Virus, Feline Leukemia Virus, Walleye Dermal Sarcoma Virus, Human T-Lymphotropic Virus, and Human Immunodeficiency Viruses (HIV). HIV can be any strain, form, subtype or variation in the HIV family.

The target molecules involved in protein synthesis in pathogen cells may bind to any portion of a tRNA molecule, for example the TΨC-loop, the D-loop, and/or the anticodon stem loop. For example, target molecules such as aminoacyl synthetases, methyl transferases and pseudouridine synthases may bind to the pathogen's TΨC-loop, D-loop or ASL or combinations thereof to initiate the particular protein reaction. A partial list of target molecules, their function and related pathogen are provided in Table 1.

TABLE 1

| Target Molecule | Function | Gene Product | Pathogen |
|---|---|---|---|
| Protein | Aminoacyl tRNA Synthetase | Essential | Bacterial/Fungal |
| Protein | Methyl transferase | Essential | Bacterial/Fungal |
| Protein | Pseudouridine synthase | Essential | Bacterial/Fungal |
| Protein | tRNA sulfurtransferase | Essential | Bacterial/Fingal |
| Protein | tRNA thiolase (ThiI) | Essential | Bacterial/Fungal |
| Protein | tRNA-guanine transglycosylase | Essential in some pathogens | Bacterial/Fungal |
| Nucleic Acid (RNA) | 5 S Ribosomal RNA | Essential | Bacterial/Fungal |
| Nucleic Acid (RNA) | Transfer RNA | Essential | Bacterial/Fungal |
| Nucleic Acid (RNA) | Viral RNA | Non-Essential | Lentiviruses, HCV |

Thus, the disclosure provides a method of identifying an inhibitor of tRNA-target molecule interactions. The method comprises forming a mixture of a nucleic acid molecule comprising a tRNA TΨC-loop fragment having at least one modified nucleotide, a target molecule that is capable of binding to the tRNA TΨC-loop fragment, and a test compound. The resulting mixture is incubated under conditions that allow binding of the tRNA TΨC-loop fragment and the target molecule in the absence of the test compound. The method further involves detecting whether the test compound inhibits the binding of the tRNA TΨC-loop fragment to the target molecule, where the absence of binding of the tRNA TΨC-loop fragment and the target molecule is indicative of the test compound being an inhibitor of tRNA-target molecule interaction. In one aspect, the detection involves the use of labels to detect the inhibition of binding of the tRNA fragment to a target molecule.

The mixture may also contain a second nucleic acid molecule that contains an anticodon stem-loop sequence. The second nucleic acid molecule may also contain one or more modified nucleotides. The second nucleic acid molecule may be linked to the first nucleic acid molecule and may facilitate binding of the TΨC-loop fragment to the target molecule in the absence of the test compound.

The nucleic acid molecule may be attached to a microarray to provide for a high-throughput assay for use in identifying such inhibitors.

In one aspect, a method of identifying an inhibitor of tRNA-target molecule interactions is also provided, where the method comprises forming a mixture of a nucleic acid molecule comprising a tRNA D-loop fragment having at least one modified nucleotide, a target molecule that is capable of binding to the tRNA D-loop fragment, and a test compound. The resulting mixture is incubated under conditions that allow binding of the tRNA D-loop fragment and the target molecule in the absence of the test compound. The method further involves detecting whether the test compound inhibits the binding of the tRNA D-loop fragment to the target molecule, where the absence of binding of the tRNA D-loop fragment and the target molecule is indicative of the test compound being an inhibitor of tRNA-target molecule interaction. In one aspect, the detection involves the use of labels to detect the inhibition of binding of the tRNA fragment to a target molecule.

In one aspect, a method of identifying an inhibitor of binding of a tRNA to a target nucleic acid molecule comprises forming a mixture containing a tRNA ASL fragment, a target nucleic acid molecule that is capable of binding to the tRNA fragment, and a test compound. The resulting mixture is incubated under conditions that allow binding of the tRNA fragment and the target nucleic acid in the absence of the test compound. The method further involves detecting whether the test compound inhibits the binding of the tRNA fragment to the target nucleic acid, where binding of the tRNA ASL fragment and the target nucleic acid molecule is indicative of the test compound being an inhibitor of binding of a tRNA to a target nucleic acid molecule. In one aspect, the detection involves the use of labels to detect the inhibition of binding of the tRNA fragment to the target nucleic acid molecule.

The disclosure also provides a method of identifying an inhibitor of tRNA-target molecule interactions, where the method comprises forming a mixture of a nucleic acid molecule comprising a tRNA D-loop fragment having at least one modified nucleotide, a tRNA ASL fragment, a target molecule that is capable of binding to the tRNA D-loop and/or ASL fragment, and a test compound. The tRNA ASL fragment may also contain one or more modified nucleotides. The resulting mixture is incubated under conditions that allow binding of the tRNA D-loop fragment and/or the ASL fragment and the target molecule in the absence of the test compound. The method further involves detecting whether the test compound inhibits the binding of the tRNA D-loop fragment and/or ASL fragment to the target molecule, where the absence of binding of the tRNA D-loop fragment and/or ASL fragment and the target molecule is indicative of the test compound being an inhibitor of tRNA-target molecule interaction. In one aspect, the detection involves the use of labels to detect the inhibition of binding of the tRNA fragment to a target molecule.

In one aspect, the tRNA D-loop fragment and the ASL fragment may be combined in a single RNA molecule, or may be used as separate nucleic acid molecules in the mixture. Where the D-loop fragment and the ASL fragment are contained in a single RNA molecule, the D-loop and the ASL may be in any arrangement, including the naturally occurring arrangement and a non-naturally occurring arrangement.

In one aspect, a method of identifying an inhibitor of tRNA-target molecule interactions comprises forming a mixture of a nucleic acid molecule comprising a tRNA TΨC-loop fragment having at least one modified nucleotide, a tRNA ASL fragment, a target molecule that is capable of binding to the tRNA TΨC-loop fragment and/or the ASL fragment, and a test compound. The resulting mixture is incubated under conditions that allow binding of the tRNA TΨC-loop fragment and/or the ASL fragment and the target molecule in the absence of the test compound. The method further involves detecting whether the test compound inhibits the binding of the tRNA TΨC-loop fragment and/or ASL fragment to the target molecule, where the absence of binding of the tRNA TΨC-loop fragment and/or ASL fragment and the target molecule is indicative of the test compound being an inhibitor of tRNA-target molecule interaction. In one aspect, the detection involves the use of labels to detect the inhibition of binding of the tRNA fragment to a target molecule.

In one aspect, the tRNA TΨC-loop fragment and the ASL fragment may be combined in a single RNA molecule, or may be used as separate nucleic acid molecules in the mixture. Where the TΨC-loop fragment and the ASL fragment are contained in a single RNA molecule, the TΨC-loop and the ASL may be in any arrangement, including the naturally occurring arrangement and a non-naturally occurring arrangement.

In one aspect, a method of identifying an inhibitor of tRNA-target molecule interactions comprises forming a mixture of a nucleic acid molecule comprising a tRNA TΨC-loop fragment having at least one modified nucleotide, a D-loop fragment, and a tRNA ASL fragment, a target molecule that is capable of binding to the tRNA TΨC-loop fragment and/or D-loop fragment and/or the ASL fragment, and a test compound. The resulting mixture is incubated under conditions that allow binding of the tRNA TΨC-loop fragment and/or D-loop fragment and/or the ASL fragment and the target molecule in the absence of the test compound. The method further involves detecting whether the test compound inhibits the binding of the tRNA TΨC-loop fragment and/or D-loop fragment and/or ASL fragment to the target molecule, where the absence of binding of the tRNA TΨC-loop fragment and/or D-loop fragment and/or ASL fragment and the target molecule is indicative of the test compound being an inhibitor of tRNA-target molecule interaction. In one aspect, the detection involves the use of labels to detect the inhibition of binding of the tRNA fragment to a target molecule. The TΨC-loop fragment, D-loop fragment and ASL may be in separate nucleic acid molecules, or may be linked on a single nucleic acid molecule, and may in any arrangement, such as the naturally occurring arrangement or non-naturally occurring arrangement.

The disclosure also provides methods for identifying inhibitors of Category B bacteria infection. Such methods comprise forming a mixture containing a tRNA fragment from a Category B Bacteria having one or more modified nucleotide bases, a target molecule from a Category B Bacteria capable of binding to the tRNA fragment, and a test compound. The resulting mixture is incubated under conditions that allow binding of the tRNA fragment and the target molecule in the absence of the test compound. The method further involves detecting whether the test compound inhibits the binding of the tRNA fragment to the target molecule. In one aspect, the detection involves the use of labels to detect the inhibition of binding of the tRNA fragment to the target molecule, where the inhibition indicates that the test compound is capable of inhibiting infection of a host cell by category B bacteria. The target molecule from a Category B Bacteria may be an aminoacyl tRNA synthetase, a methyl transferase, a pseudouridine synthase, a ribosomal RNA (e.g. 5S ribosomal RNA), or a transfer RNA.

In another aspect, the disclosure provides methods for identifying inhibitors of aminoacyl-tRNA synthetases (AaRS) for use as antimicrobial agents. In one aspect, criteria for such inhibitors also include: i) diversity between prokaryotic and eukaryotic sequences to develop inhibitors that selectively target the prokaryote; ii) conserved targets across different pathogens for development of broad spectrum antimicrobial compounds; iii) 20 potential targets as each amino acid has its own AaRS; iv) target molecules that are soluble, stable, and relatively easy to purify for use in an HTS; and v) X-ray crystal structures. In another aspect, the target molecule may be an essential gene for bacterial growth and/or propagation. For bacterial pathogens modified nucleotides at position 34 of the tRNA may be important for tRNA-AaRS binding. For example, in GluRS binding, a modified nucleotide at position 34 may be important for efficient charging of the tRNA in bacteria for binding to the synthetase.

In one aspect, the AaRS is LysRS. In addition to this being an essential enzyme, LysRS from bacteria utilizes a different modified nucleotide base and RNA sequence in the anticodon stem loop than mammals. LysRS has been isolated and purified from many species indicating that this enzyme is soluble, stable, and relatively easy to isolate. The crystal structure of LysRS has been solved for several bacteria. In addition, enzyme homology of LysRS of human to the food and water borne bacteria is less than 10% (FIGS. 1A-D, Table 2). The homology for LysRS among the bacteria may range from approximately 20% to nearly 100%. Thus, in one aspect, inhibitors identified by these methods inhibit the binding of bacterial AaRS to the bacterial tRNA, but does not inhibit the mammalian AaRS to the mammalian tRNA.

TABLE 2

|  | Shi | E C | Sal | Yer | Lis | Cam | Vib | H S |
|---|---|---|---|---|---|---|---|---|
| Shigella flexneri | 1.00 | 0.99 | 0.95 | 0.86 | 0.5 | 0.46 | 0.19 | 0.08 |
| Escherichia coli | 0.99 | 1.00 | 0.95 | 0.86 | 0.5 | 0.46 | 0.19 | 0.08 |
| Salmonella enterica | 0.95 | 0.95 | 1.00 | 0.85 | 0.5 | 0.45 | 0.18 | 0.08 |
| Yersinia enterocolitica | 0.86 | 0.86 | 0.85 | 1.00 | 0.48 | 0.47 | 0.19 | 0.07 |
| Listeria monocytogenes | 0.5 | 0.5 | 0.5 | 0.48 | 1.00 | 0.45 | 0.2 | 0.09 |
| Campylobacter jejuni | 0.46 | 0.46 | 0.45 | 0.47 | 0.45 | 1.00 | 0.19 | 0.07 |
| Vibrio cholerae | 0.19 | 0.19 | 0.18 | 0.19 | 0.2 | 0.19 | 1.00 | 0.07 |
| Homo sapiens | 0.08 | 0.08 | 0.08 | 0.07 | 0.09 | 0.07 | 0.07 | 1.00 |

In another aspect, the methods may involve the detection of the binding of the test compound to the tRNA fragment, the target molecule, or both the tRNA fragment and the target molecule. In one aspect, the binding of the test compound is indicative of the test compound being an inhibitor of bacterial propagation, bacterial infection, protein synthesis, or tRNA binding.

In another aspect, methods for diagnosing (or assisting in diagnosing) whether a subject has an infectious disease are also provided. Such methods may be used to diagnose (or assist in diagnosis) of any infectious disease, including, but not limited to bacterial diseases, viral diseases, and fungal diseases.

Thus, in one aspect, a method for diagnosing (or assisting in diagnosing) whether a subject has a bacterial infection is provided. The method comprises forming a mixture comprising a first RNA molecule having at least one modified nucleotide and a biological sample obtained from a subject. The mixture is then incubated under conditions that allow the interaction, or binding, of the first RNA molecule and a target molecule in the biological sample, then detecting whether or not the first RNA molecule binds to the target molecule in the biological sample. Binding of the first RNA molecule and the target molecule is indicative of the positive diagnosis of a bacterial infection. The lack of binding of the RNA molecule and the target molecule is indicative of the negative diagnosis of a bacterial infection.

In another aspect, a method for identifying target molecules that bind to nucleic acid molecules having one or more modified nucleotides is provided. The methods generally comprise forming a mixture of a biological sample from a subject and at least one nucleic acid molecule derived from, or corresponding to, a tRNA loop having at least one modified nucleotide. The mixture is incubated under conditions that allow binding of a target molecule in the biological sample to the first nucleic acid molecule. After the incubation, target molecules that bind to the nucleic acid molecule can be detected. A washing step may also be used to remove unbound molecules and facilitate the detection of the bound molecules. The tRNA loop molecules that can be used in the mixture include those selected from the group consisting of a TψC-loop, a D-loop, and an anticodon loop, and combinations thereof.

The tRNA loop molecules may be derived from or correspond to tRNA sequences from any organism. For example, tRNA loop molecules for use in the methods may be derived from, or correspond to, tRNA sequences from bacterial, fungal, or viral pathogens, and may incorporate modified nucleotides based on the particular pathogen.

The nucleic acid molecules may be arranged on an array to allow for the development of high throughput assays for the detection of molecules that bind to nucleic acid molecules having a modified nucleotide. Such arrays may contain multiple nucleic acid molecules derived from tRNA TψC-loop fragments, D-loop fragments, and anticodon loop fragments, to allow for the simultaneous screening of one or more different nucleic acid sequences having one or more different modified nucleotides. The one or more different nucleic acid sequences may be derived from or correspond to sequences from a single pathogen or a group of pathogens to identify target compounds for which broad spectrum inhibitors may be identified. In addition, the nucleic acid molecules may be detectably labeled to further facilitate detection of the binding of a target molecule to a tRNA molecule.

Such methods may be useful in the development of diagnostic methods to detect whether a subject is infected with a particular pathogen. In addition, molecules that are identified as binding to the tRNA loop molecules by such methods can be used in inhibition assays as disclosed herein to identify compounds useful for the inhibition of pathogen infection in a subject. Such compounds may be useful as therapeutic compounds or in the development of therapeutic compounds for the treatment of pathogen infections.

The methods for detecting binding of the target molecule to the tRNA or the inhibition of such binding or the diagnostic methods may be performed using any method for such detection, for example, the AlphaScreen® assay (Packard Instrument Company, Meriden, Conn.). AlphaScreen® technology is an "Amplified Luminescent Proximity Homogeneous Assay" method utilizing latex microbeads (250 nm diameter) containing a photosensitizer (donor beads), or chemiluminescent groups and fluorescent acceptor molecules (acceptor beads). Upon illumination with laser light at 680 nm, the photosensitizer in the donor bead converts ambient oxygen to singlet-state oxygen. The excited singlet-state oxygen molecules diffuse approximately 250 nm (one bead diameter) before rapidly decaying. If the acceptor bead is in close proximity to the donor bead (i.e., by virtue of the interaction of the target molecule and RNA molecule), the singlet-state oxygen molecules react with chemiluminescent groups in the acceptor beads, which immediately transfer energy to fluorescent acceptors in the same bead. These fluorescent acceptors shift the emission wavelength to 520-620 nm, resulting in a detectable signal. Antagonists of the interaction of the target molecule with the RNA molecule will thus inhibit the shift in emission wavelength, whereas agonists of this interaction would enhance it.

The disclosed methods may be performed by mixing the component nucleotides (e.g. the RNA molecule), the target molecule and the test compound in any order, or simultaneously. For example, a target molecule may be first combined with a test compound to form a first mixture, and then an RNA molecule may be added to form a second mixture. In another example, a target molecule, an RNA molecule and the test compound may all be mixed at the same time before incubation. In one aspect, the mixture is incubated under conditions that allow binding of the RNA molecule and the target molecule in the absence of the test compound.

The inhibition of binding of the RNA molecule and the target molecule by the test compound may be detected using any method available for the detection of inhibition. In one aspect, the determining step may be performed using methods including, but not limited to, gel shift assays, chemical and enzymatic footprinting, circular dichroism and NMR spectroscopy, equilibrium dialysis, or in any of the binding detection mechanisms commonly employed with combinatorial libraries of probes or test compounds. The inhibition of binding indicates that the test compound may be useful for inhibiting the interaction between an RNA molecule and a target molecule.

Any compound may be tested using the methods of the present invention to identify compounds capable of inhibiting interactions between an RNA and a target molecule. Test compounds that may be screened with methods of the present invention include, but are not limited to, polypeptides, beta-turn mimetics, polysaccharides, phospholipids, hormones, prostaglandins, steroids, aromatic compounds, heterocyclic compounds, benzodiazepines, oligomeric N-substituted glycines, oligocarbamates, polypeptides, saccharides, fatty acids, steroids, purines, pyrimidines, derivatives, structural analogs or combinations thereof. Some test compounds are synthetic molecules while others are natural molecules.

Test compounds may be obtained from a wide variety of sources including libraries of synthetic or natural compounds. Combinatorial libraries can be produced for many types of compound that can be synthesized in a step-by-step fashion. Large combinatorial libraries of compounds can be constructed by the encoded synthetic libraries (ESL) method described in WO 95/12608, WO 93/06121, WO 94/08051, WO 95/35503 and WO 95/30642. Peptide libraries can also be generated by phage display methods (see, e.g., Devlin, WO 91/18980). Libraries of natural compounds in the form of bacterial, fungal, plant and animal extracts can be obtained from commercial sources or collected in the field. Known pharmacological agents can be subject to directed or random chemical modifications, such as acylation, alkylation, esterification, amidification to produce structural analogs.

Combinatorial libraries of peptides or other compounds can be fully randomized, with no sequence preferences or constants at any position. Alternatively, the library can be biased, i.e., some positions within the sequence are either held constant, or are selected from a limited number of possibilities. For example, in some cases, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, or to purines.

In another aspect, the test compounds may be naturally occurring proteins or their fragments. Such test compounds may be obtained from a natural source, e.g., a cell or tissue lysate. Libraries of polypeptide agents may also be prepared, e.g., from a cDNA library commercially available or generated with routine methods. The test compounds can also be peptides, e.g., peptides of from about 5 to about 30 amino acids, with from about 5 to about 20 amino acids being preferred and from about 7 to about 15 being particularly preferred. The peptides can be digests of naturally occurring proteins, random peptides, or "biased" random peptides. In some methods, the test compounds are polypeptides or proteins.

In another aspect, the test compounds may be nucleic acids. Nucleic acid test compounds may be naturally occurring nucleic acids, random nucleic acids, or "biased" random nucleic acids. For example, digests of prokaryotic or eukaryotic genomes may be similarly used as described above for proteins.

In some preferred methods, the test compounds are small molecules, e.g., molecules with a molecular weight of not more than about 500 or 1,000. Preferably, high throughput assays are adapted and used to screen for such small molecules. In some methods, combinatorial libraries of small molecule test compounds as described above can be readily employed to screen for small molecule modulators of retroviral propagation. A number of assays are available for such screening, e.g., as described in Schultz et al., Bioorg Med Chem Lett 8:2409-2414, 1998; Weller et al., Mol Divers. 3:61-70, 1997; Fernandes et al., Curr Opin Chem Biol 2:597-603, 1998; and Sittampalam et al., Curr Opin Chem Biol 1:384-91,1997.

The invention also comprises kits and compositions (e.g., reaction mixtures, etc.) for a method of the invention. A kit is a combination of individual compositions useful or sufficient for carrying out one or more steps of a method of the invention, wherein the compositions are optimized for use together in the method. A composition comprises an individual component for at least one step of a method of the invention. The present disclosure further provides a kit for screening for an inhibitor of interactions between an RNA molecule and a target molecule, comprising: an RNA fragment and a reagent for detection of binding to a target molecule, such as a detectable label. In some embodiments, the kit also comprises one or more target molecule(s) that are capable of binding to the RNA fragment. In some embodiments, the kit further comprises additional reagents for conducting the screening methods. In some embodiments, the kit further comprises a plurality of inhibitors of retroviral reverse transcription. In some embodiments, the reagent comprises a dye that undergoes fluorescence enhancement upon binding to nucleic acids (e.g., the dye is RIBOGREEN, SYBR Gold, SYBR Green I, or SYBER Green II). In some embodiments, the kit further comprises control reagents (e.g., sample polymerases and/or inhibitors for positive controls, polymerase and/or inhibitor minus samples for negative controls, etc.). In some embodiments, the kit further comprises instructions for carryout out the methods. In some embodiments, the instructions are embodied in computer software that assists the user in obtaining, analyzing, displaying, and/or storing results of the method. The software may further comprise instructions for managing sample information, integrating with scientific equipment (e.g., detection equipment), etc.

Also provided are kits for identifying inhibitors bacterial infection. In one aspect, the kits include, a tRNA fragment and a detectable label for detecting the interaction of the tRNA fragment and a target molecule from a biological sample. The kits of the present invention may also include target molecules, and/or reagents for performing the assays. The kits may also include labeling components for detecting whether a test compound inhibits the binding of the fragment tRNA and the target molecule.

Also provided are kits for diagnosing whether a subject is infected with an infectious disease. Such kits comprise: an RNA fragment and a reagent for detection of binding to a target molecule from a biological sample (such as a detectable label).

The invention will be further explained by the following illustrative examples that are intended to be non-limiting.

EXAMPLES

Example 1

Synthesis of RNA Sequences Having Modified Nucleotides

The first step in producing the fragment RNA molecule sequences is the synthesis of the modified nucleotides, also known as phosphoramidites (Agris et. al *Biochimie*. (1995) 77(1-2):125-34). The modified nucleotides are then used during the synthesis of the RNA oligomers (Ogilvie et. al. *Proc Natl Acad Sci USA*. (1988) 85:5764-8). Synthetic approaches overcome the substantial barrier of obtaining sufficient amounts of natural products for the functional characterization studies. In addition to providing the fully modified RNA for characterization of the fragment tRNA:target molecule binding, the synthetic approach allows for the preparation of intermediate steps/forms of the modified material that can further elucidate the individual contribution of each modification step in enhanced tRNA binding.

Modified base nucleic acid molecules were prepared using a combination of methods for the synthesis, incorporation, and purification of all the modified nucleotides. Modified base phosphoramidites were prepared using known methods, such as those disclosed in Ogilive et. al., *Proc. Natl. Acad. Sci., U.S.A.* , 85:5764-5768 (1988). S ($mnm^5s^2U$) was prepared following the previously published procedures of Vorbruggen et. al., *Angew. Chem.*, 14: 225-256(1975). 6 ($t^6A$) and $ ($cmnm^5s^2U$) were synthesized following the procedures described below. Pseudouridine is commercially available and was incorporated into the RNA oligomers using the methods described below. Functional groups on the modified nucleotide bases were protected using phosphoramidite chemistry (Ogilvie et. al., 1988). Using this chemistry, over 20 different modified nucleotides have been incorporated into a range of oligonucleotides ranging in length from 3 to 36 nucleotides (Nobles, et. al., *Nuc. Acids Res.*, 30: 4751-4760 (2002)). The addition of a protecting group to each modified base and ribose is described below. The protecting group was subsequently removed after synthesis of the RNA oligomer. While 2 position thio-groups can be oxidized in standard RNA synthesis protocols this barrier has been overcome by using the tert-butyl hydroperoxide (10% solution in acetonitrile) oxidizing agent (Kumar and Davis, *Nuc. Acids Res.*, 25(6): 1272-1280 (1997)).

Compound 1—$mnm^5s^2U$ Phosphoramidite

Base protection of $mnm^5s^2U$ [5-(N-trifiluoroacetyl)methylaminomethy 2-thiouridine]: The 2,2,2-trichloroethoxycarbonyl protecting groups were used to protect exo-amino function of the nucleotide. The nucleotide is treated with excess of trifluoroacetic anhydride in pyridine solution, followed by selective removal of trifluoroacetyl groups from sugar moiety with 10% sodium bicarbonate giving the base protected product (Malkiewicz, *Tetrahedron Letters*, 24: 5387-5390 (1983)).

Protection of the ribose and phosphitylation follow the general scheme:

Base Protection of $mnm^5s^2U$

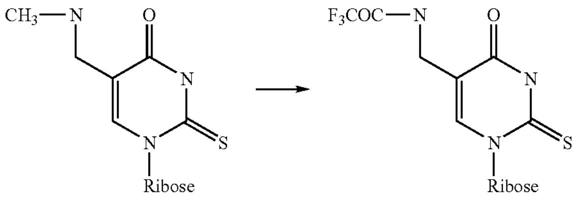

Compound 2—$t^6A$ Phosphoramidite

Preparation of the $N^6$-(N-threonylcarbonyl)adenosine for automated synthesis follows a slightly different approach than that for the other phosphoramidites. First, the ribose functions of adenosine are protected following the methods outlined above. Next, the ribose protected adenosine was reacted with 3 equivalents of phenoxycarbonyltetrazole in anhydrous dioxane for 18 hr at 37° C. to produce phenyl carbamates at the six position. This was followed by aminolysis with 3 equivalents of crystalline L-threonine p-nitrobenzyl ester in anhydrous dioxane, for 18 hr at 37° C., producing the N6-(N-threonylcarbonyl)adenosine. The t6A carboxylate was then protected by a trimethylsilylethyl group, in a manner similar to that used to protect the ribose function. Finally the phosphoramidite was phosphitylated following the protocol described below.

Modification of Adenosine to t6A

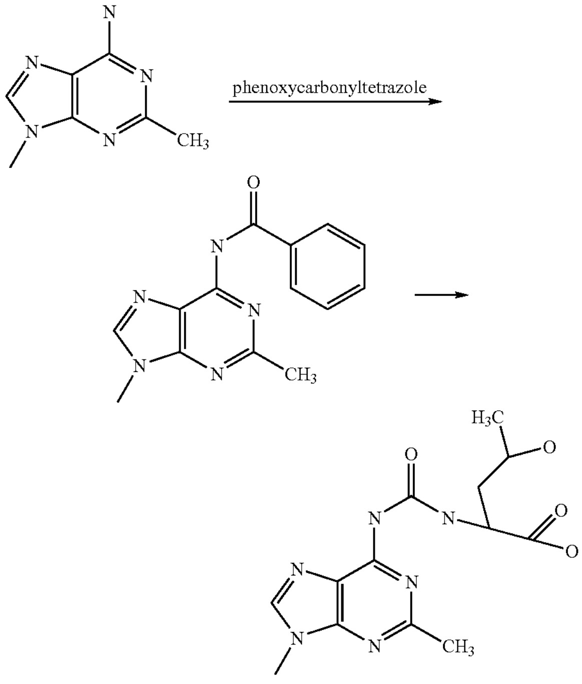

Compound 3—$cmnm^5s^2U$ Phosphoramidite

Preparation of the $cmnm^5s^2U$ nucleotide follows published methods (Reese and Sanghvi, *J. Chem. Soc. Chem. Commun.*, 62-63 (1984)). Briefly, 2 thiouridine was heated with 5 molar equivalents each of pyrrolidine and formaldehyde in aqueous solution for 1 h, under reflux to produce 2',3'-O-isopropylidene-5-pyrrolidinomethyl-2-thiouridine. This base was treated with 10 mol. equivalents of methyl iodide in acetonitrile at room temperature. After 16 hours, the products were concentrated under reduced pressure to give the putative niethiodide which was then dissolved in acetonitrile and allowed to react with 3 molar equivalents of glycine t-butyl ester at room temperature for 16 h. This product was then purified and protection of the ribose and phosphitylation follow the general scheme:

Preparation and Base Protection of cmnm5s2U

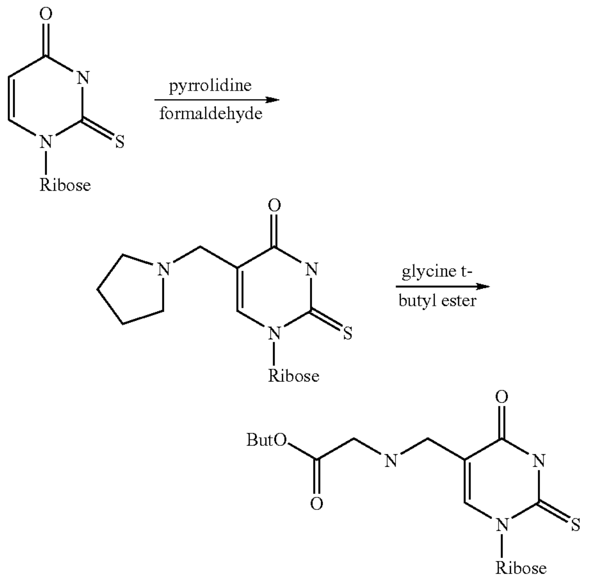

General procedure for ribose protection and phosphitylation prior to RNA oligomer synthesis: After base protection the scheme for the synthesis of 5'-O-(4,4'-dimethoxytrityl)-2'-O-tertbutyidimethylsilyi-modified ribonucleoside-3'-O-(2-cyanoethyl-N-diisopropyl)-phosphoramidites is the same for all modified nucleotides. The protected nucleoside was dried by co-evaporation twice with pyridine and dissolved in pyridine. Tert-butyldimethylchlorosilane and imidazole were added and reacted for 4 hours at room temperature. The excess silyl chloride was decomposed with water and dichloromethane. The aqueous layer was extracted twice with dichloromethane and combined with the organic layer. The solvent was evaporated by vacuum yielding a gum which was dissolved in ether and precipitated by pouring slowly into petroleum ether (40-60° C.) with stirring. The precipitate was collected and washed twice with petroleum ether. At this point the crude product contains three components; the 2',3' disilylated, 2' silylated (major product) and 3' silylated. The pure 2' protected isomer were obtained by silica gel column chromatography. This product is then ready for phosphitylation.

The N-protected-5'-O-dimethoxytrityl-2'-O-tert-butyldimethylsilyl-ribonucleosides was dried by two co-evaporations with anhydrous pyridine and THF. The residue was dissolved in anhydrous THF under argon. Dimethylaminopyridine, N,N,N-ethyidiisopropylamine and cyano-ethoxydi-isopropy amino-chlorophosphine were added through a rubber septum. After 2 hours the reaction mixture was quenched with ethyl acetate and washed with 5% sodium bicarbonate followed by water. Aqueous washes were back extracted with ethyl acetate. Combined organic layers were dried over sodium sulphate. Solvent was evaporated yielding a viscous oil. The product was co-evaporated twice with toluene and the pale yellow phosphoramidite products were purified by flash silica gel chromatography.

Generalized Sugar Protection and Phosphinylation of Modified Nucleotides

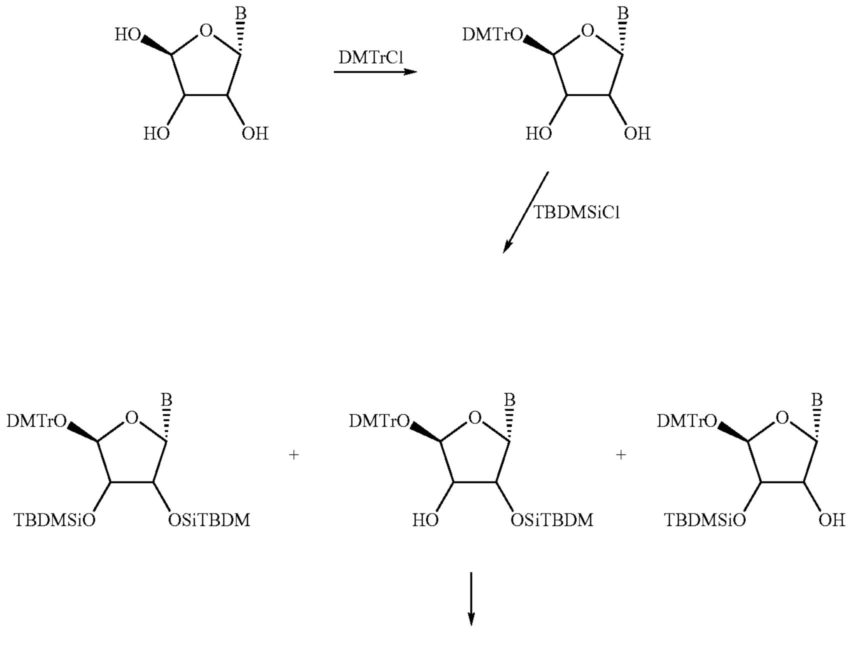

-continued

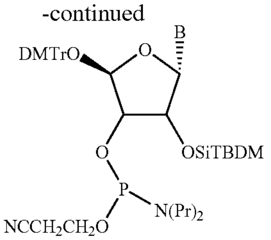

The protecting group is subsequently removed after synthesis of the RNA oligomer. The addition of a protecting group to each modified base and ribose is described. While 2 position thio-groups can be oxidized in standard RNA synthesis protocols this has been overcome by using the tert-butyl hydroperoxide (10% solution in acetonitrile) oxidizing agent (Kumar and Davis, 1997).

The modified bases were incorporated into the 17 residue tRNA oligomers based on 7 food and water borne bacteria from the Category B priority pathogen list (Table 2, S=mnm5s2U; 6=t6A; $=cmnm5s2U; P=pseudouridine) along with a random 17mer oligomer to be used as a negative control. In those cases where the actual oligomer sequence was not fully determined (S or $ in Table 3) both sequences were synthesized and tested. Each oligomer was tagged with a fluorescent dye for use in the assays and diagnostic. In addition, a subset of the oligomers were synthesized with a thiol group on the 3' end and a different dye for attachment to the microarray chips. For the microtiter plate format each oligomer was tagged with fluorescent dye on the 3' end. Purity of the oligomers was confirmed by gel electrophoresis and proper incorporation of the modified nucleotide bases was confirmed by mass spectrometry.

than the native RNA oligomer or the unmodified RNA oligomer with no modified nucleotide bases (FIG. 2).

To determine binding affinity, an assay of ASL for yeast $tRNA^{phe}$ was prepared varying only in the number of post-transcriptional nucleotide base modifications. This array was probed using a peptide from a phage display library that bound to an ASL containing 3 modifications. The affect of modification on the affinity of a peptide to an RNA substrate-sequence (Sequence A in FIG. 2: 5'-CCAGACUGAA-GAUCUGG)(SEQ ID NO: 18) is the primary unmodified yeast $ASL^{Phe}$. Sequence B in FIG. 2 (5'-CCAGACmUGm AAGAUm$^5$CUGG)(SEQ ID NO: 19) is a template ASL sequence indicating the locations of the modified nucleotides for the various combinations of modified nucleotide bases in the mimics of the anticodon stem loop. Sequence C in FIG. 2 (5'-CCAGACmUGmAAm1GAψm$^5$CUGG)(SEQ ID NO: 20) is the sequence of the native yeast $tRNA^{phe}$. Sequence D in FIG. 2 (5'- GGUCUAGAA GmUCmAGACC)(SEQ ID NO: 21) is a secondary structure for the doubly modified Phe ASL sequence that's has a propensity to form a duplex. When the affinity of the peptide to the ASLs was determined it was found that the modifications affected the affinity by more than 3 orders of magnitude (FIG. 2). This assay also demonstrates

TABLE 3

| (SEQ ID NOS 9-17), respectively in order of appearance): | | | | | | | | | | | | | | | | | |
|---|---|---|---|---|---|---|---|---|---|---|---|---|---|---|---|---|---|
| *E. Coli* | G | U | U | G | A | C | U | S | U | U | 6 | A | P | C | A | A | U |
| *Salmonella* | G | U | U | G | A | C | U | S | U | U | 6 | A | P | C | A | A | U |
| *Shigella* | G | U | U | G | A | C | U | S | U | U | 6 | A | P | C | A | A | U |
| *Camptobacteria* | U | C | U | C | C | C | U | Sor$ | U | U | 6 | A | G | G | A | G | G |
| *Vibrio* | G | U | U | G | G | C | U | Sor$ | U | U | 6 | A | C | C | A | A | U |
| *Listeria* 1 | U | C | U | G | A | C | U | Sor$ | U | U | 6 | A | P | C | A | G | A |
| *Listeria* 2 | G | C | U | G | A | C | U | C | U | U | 6 | A | P | C | A | G | C |
| *Yersinia* 1 | C | U | U | G | A | C | U | S | U | U | 6 | A | P | C | A | A | U |
| *Yersinia* 2 | C | U | U | G | A | C | U | C | U | U | 6 | A | P | C | A | A | U |

Example 2

Inhibitor Screening Assay

A set of experiments was conducted to identify an RNA oligomer substrate to be used in an assay to identify substrates for use in identifying inhibitors of tRNA binding to a phenylalanine synthetase from yeast. A peptide was first identified for use as a phenylalanine synthetase mimic. The peptide was labeled with a fluorescent peptide for use in detection in binding assays.

A series of RNA oligomer substrates were also synthesized containing modified nucleotides (FIG. 2). A 17mer RNA oligomer containing the modified nucleotide bases Cm, Gm, and m5C was identified as having a greater affinity for a fluorescent peptide that mimics phenylalanine synthetase the significance of the effect of the modified nucleotides on binding between the enzyme and its RNA substrate. Such an assay may be used to identify inhibitors of $tRNA^{phe}$ binding to phenylalanine synthetase.

Example 3

Lysine Synthetase Inhibitor Assay

A set of assays can be developed to target LysRS that is unique to each of the Category B Bacteria and can be based on microtiter plate technology. In addition, assays can be developed to utilize microarray technology for the development of a multidimensional HTS assay that incorporates a subset of 7 of the individual HTS assays onto a single microarray chip. A diagnostic assay can also use the microarray technology, but in a format tailored to diagnostic applications. The microtiter based and microarray based HTS assays can then be used to screen compound libraries for active compounds that can be developed as a narrow-spectrum organism specific antibiotics and as a broad-spectrum antibiotic.

RNA oligomers are produced incoporating modified nucleotide bases, $mnm^5s^2U$, $cmnm^5s^2U$, $t^6A$, and P. The modified bases are incorporated into the 17 residue tRNA oligomers in Table 3 along with a random 17mer oligomer to be used as a negative control. In those cases where the actual oligomer sequence has not been fully determined (S or $ in Table 3) both sequences are synthesized and tested. Each oligomer is tagged with a fluorescent dye for use in the assays and diagnostic. In addition, a subset of the oligomers is synthesized with a thiol group on the 3' end and a different dye for attachment to the microarray chips. For the microtiter plate format each oligomer is tagged with fluorescent dye on the 3' end. The RNA oligomers are synthesized and purified following protocols developed specifically for these modified reagents (Agris et. al., Biochimie, 77(1-2):125-134 (1995), Murphy et. al., Nat. Struct. Mol. Biol., (12):1186-1191 (2004)). Purification of the oligomers is performed by HPLC as described (Agris et. al., Acta Biochim Pol., 46(1):163-172 (1999)). Purity of the oligomers is confirmed by gel electrophoresis and proper incorporation of the modified nucleotide bases is confirmed by mass spectrometry.

LysRS corresponding to each of the 7 organisms will be over expressed in and isolated from *E. coli* using previously described methods (Madore et. al., FEBS Journal, 266:1125-1135 (1999)). A BAC clone containing the LysRS gene can be obtained. The LysRS is encoded from nucleotides from each of the organisms and is available on a BAC clone (Table). From the BAC a subclone can be used to generate an expression vector for production of the Lysine Synthetase enzyme. The production of active LysRS enzyme can be performed using published protocols (e.g. Madore et. al.).

(Millar, Curr. Opin. Struct. Biol., 6:637-642 (1996)). Time-resolved fluorescence detection allows for monitoring complex formation and inhibition in solution. Affinity of each of three or four oligomers for each LysRS: modified $ASL^{Lys}$; unmodified $ASL^{Lys}$; and, the negative random control can be determined by monitoring the change in fluorescence.

The enzyme and tRNA interactions can be monitored using time resolved fluorescence spectroscopy to effectively monitor the binding of tRNA to the synthetase (Lam, Biochemistry, 14:2775-2780 (1975)). tRNA synthetase binding can be characterized by monitoring the quenching of tryptophan residues in the protein. While several of the target organism synthetases contain a tryptophan that could be used to monitor tRNA binding, for uniformity the LysRSs is labeled using fluorescein isothiocyanate, FITC (Pierce, Rockford Ill.), as described, for example, by Commans, J. Mol. Biol., 253:100-113 (1995). The association of tRNA for its cognate synthetase is strong (Ka=1×10 6) and specific with non-cognate tRNA Ka 1 to four orders of magnitude lower. While measuring total fluorescence is sufficient to monitor complex formation, integration of time resolved fluorescence detection allows for monitoring both free and bound species in the interaction (Jager, Curr. Pharma. Biotech., 4:463-476 (2003)). Time resolved measurements monitor an intrinsic molecular property which results in high statistical accuracy and may make fluorescence lifetime analysis (FLA) more appropriate for HTS applications (Jager). Titrations studies 100 nM of enzyme solution can be used to monitor complex formation (Commans 1995). To determine the amount of ASL to add per reaction a titration of the ASL can be made. The starting solution conditions for the assay can be 5 mM $MgCl_2$ and 2 μM spermidine, pH 6.8. Affinity of tRNALys for the synthetase a titration of 0 to 4 μM should be sufficient to achieve complete complex formation. Initially a 96 well format can be used in method development that will be expanded to a 386 format once the assay parameters have been determined.

TABLE 4

LysRS genome for each organism is available as a BAC clone.

| Organism | Genome location | Source |
|---|---|---|
| *Salmonella enterica* | 19802-21330 | Washington University Genome Sequencing Center. St. Louis, Mo |
| *Campylobacter jejuni* | 365440-367864 | Sanger Inst. Hinxton, Cambridge, UK |
| *Listeria monocytogenes* | 35510-37065 | Institut Pasteur Paris, France |
| *Vibrio cholerae* | chromosome I, section 239 residues 7399-10352 | The Institute for Genomic Research Rockville, Maryland |
| *Escherichia coli* O157:H7 | 3838117-3841613 | Laboratory of Genetics, University of Wisconsin-Madison, Madison Wisconsin. |
| *Yersinia pseudotuberculosis* IP32953 | 3718692-3722057 | Institut Pasteur Paris, France |
| *Shigella flexneri* 2a str. 2457T | 2958664-962160 | Laboratory of Genetics, University of Wisconsin-Madison, Madison Wisconsin |

Assays can then be performed to monitor the inhibition of $ASL^{Lys}$ binding to LysRS. Such assays take advantage of the fact that modified $tRNA^{Lys}$ is a 100 fold better substrate for binding to LysRS than a $tRNA^{Lys}$ containing no modified bases (Sylver et. al., Biochemistry 32(15):3836-3841 (1995)). Monitoring of the $ASL^{Lys}$ LysRS complex formation can be determined using time-resolved fluorescent detection Two alternatives are available for time resolved fluorescence. First, is the use of alternative fluorescent dyes such as Cy3 or Cy5 which can easily be attached to each oligomer. Alternatively, an enzyme linked assay format is available where the purified LysRS can be chemically modified to add biotin which will bind to the surface of streptavidin coated well using a Mts-Atf-Biotin Label Transfer Reagent from Pierce, Rockford Ill. This will allow for the binding of the protein to the surface of each well. With the LysRS bound to surface, complex formation can be monitored.

Using the more sensitive assay protocol from above, the assay reagents and conditions can be varied and the optimum reaction mixture will be determined based on Z-factor analysis. After the optimum conditions are determined, the robustness of the assay will be verified by modifying various reagent concentrations or assay conditions by ±10% and determining Z-factor scores. These scores will be plotted and used to determine which assay conditions are most relevant to control. In parallel, positive control compounds can be tested and selected. The positive control compounds can be used during the routine use of the assay to verify that the assay is functioning properly. As part of the assay optimization experiments, the specificity and selectivity of each enzyme can be confirmed by determining the affinity for other closely related substrates (oliogomers prepared for the other LysRS).

The assays can then be used with a small number of molecular inhibitors contained in a test library supplemented with known inhibitors of LysRS along with other known positive controls to confirm the use of the assay. The test compounds, known AaRS inhibitors and positive control compounds can be aliquoted into 96-well plates at a predetermined concentration corresponding to 40 µg of compound per well. The remaining assay components can be added and the reaction allowed to proceed to completion. The reaction results can be quantified and the $IC_{50}$ calculated. A dilution series of compounds with an $IC_{50}$ less than $1 \times 10^{-5}$ M can be analyzed with this assay to confirm that the compound is active and to more accurately determine the $IC_{50}$. Those compounds that are active in this assay can be classified as 'hits' and further assayed for biological testing to determine antimicrobial activity.

For determining activity of the compounds, the following bacterial species can be tested against each sample:

*Escherichia coli* American Type Culture Collection (ATCC) 25922 as a surrogate marker for diarrheagenic *E. coli*.

*Shigella sonnei* (clinical isolate) as the most common species causing shigellosis in developed countries.

*Salmonella* serotype Enteritidis (clinical isolate) as a common and expanding global cause of salmonellosis.

*Yersinia enterocolitica* (clinical isolate) as a common cause of intestinal yersiniosis.

*Vibro cholerae* (clinical isolate) as the most important species in the genus *Vibrio* causing diarrhea.

*Campylobacter jejuni* (clinical isolate) which continues to be the most common enteric pathogen isolated from patients with diarrhea.

*Listeria monocytogenes* (clinical isolate) as the most common cause of invasive listeriosis.

As a minimum inhibitory concentration (MIC), an achievable potency of less than or equal to 32 µg/ml tested against any of the above pathogens would be considered an active compound worthy of an extended secondary screen study.

Samples can be tested using the reference broth microdilution methods recommended by the Clinical and Laboratory Standards Institute (CLSI; formerly the National Committee for Clinical Laboratory Standards [NCCLS]) M7-A7 and M45-A documents. A 96 well microtiter tray assay can be used to test a single concentration of 32 µg/ml against each pathogen. A working concentration of 64 µg/ml can be made using appropriate solvents and diluents. A calibrated pipette is used to transfer 50 µL of each sample into one well of each of three 96-well microtitre plates. A direct colony suspension is used to make a standard inoculum (equivalent to a 0.5 MacFarland standard) of each bacteria in Mueller-Hinton broth (MHB). A 50 µL aliquot of a diluted bacterial suspension in MHB (supplemented with lysed horse blood for *C. jejuni*) is added to each sample to achieve a final bacterial concentration of $3-5 \times 10^5$ CFU/ml, thus diluting the sample 1:2 to a final test concentration of 32 µg/ml. Each batch of samples includes two internal quality control antimicrobial agents with a know potency range and that target protein synthesis. A positive growth control with only growth support media and an ethanol control at concentrations equivalent to that in the samples is also tested for each pathogen concurrently. After the broth microdilution plates are inoculated and incubated in an ambient air environment at 35° C. for 20-24 hours for the enteric bacilli and *L. monocytogenes*. *C. jejuni* is incubated for 48 hours at 37° C. in a microaerobic atmosphere, using gas-generated sachets in a sealed hard plastic container. After appropriate incubation times, the plates are removed from incubation and each well inspected for growth. If a well is clear of growth (non-turbid), an MIC of $\leq 32$ µg/ml would be determined and the investigational agent therefore identified as being active A secondary screen of "active" samples includes an extended dilution series (eight to 12 $\log_2$ dilution steps) to determine "on-scale" MIC values for a potential antimicrobial agent including evaluation of breadth of spectrum against a larger collection (140 strains) of FWB pathogens listed above (20 isolates each). These isolates are recent clinical strains representing wild-type and strains with documented critical resistance phenotypes; testing methodologies to be those described above.

A multidimensional microarray HTS based on the above assay can then be developed. The multidimensional microarray HTS can be used to screen for inhibitors of each enzyme simultaneously; thus, providing a means to identify narrow spectrum inhibitors (inhibits one enzyme) or broad spectrum inhibitors (inhibits several to all of the enzymes). Each of the specific oligomers can be attached in a small grid on the microarray. After all of the oligomers are attached each enzyme is added and allowed to bind to its respective oligomer to form a substrate-enzyme complex as confirmed in the specificity and selectivity testing. A single inhibitor is then added to each grid and the active compounds will dissociate the substrate-enzyme complex as determined by measuring fluorescence.

Alternatively, rather than fluorescently labeling the bacterial proteins, a fluorophore can be attached within the RNA substrate. While the most common method to fluorescently label an oligomer is to attach it either on the 3' or 5' end; for these microarray applications attaching the fluorophore within the oligonucleotide may simplify and/or facilitate detection. A pyrrolo fluorescent cytidine analog may be used in the generation of the RNA oligonucleotides (Glen Research Sterling, Va.). This cytidine analog base pairs with other nucleotides as a normal nucleotide. Also, this fully substituted oligonucleotide has the same Tm as the control oligonucleotide.

A review of all the LysRS substrates, Table 3, finds that they all contain a cytosine in the loop at position 32 and also in the stem portion of the ASL. To determine to optimum position for placement of the cytidine analog, test oligomers can be made with both positions labeled for the *E. coli* substrate. The association constant and intensity of signal quenching can be determined for both test oligomers. Results of these experiments will determine the optimal substrate(s)

for the chip. For the remaining oligomers, the selectivity and specificity of each oligomer containing the modified nucleotide bases to their respective enzymes is confirmed in solution during the development of the HTS assays and can be verified when attached to the microarray chip. The organism specific RNA oligomers are attached to the glass microarray chip using gold-thiol methods. The thiol group is commercially available in the phosphoramidite formulation used in oligomer synthesis and is incorporated in the same chemical step fashion as individual amidites (i.e. A, U, G, C) during synthesis of the oligomers.

Each individual oligomer along with a positive and negative control will be attached to a substrate followed by addition of the enzymes. Each grid is mechanically isolated. Inhibitors are added to each grid followed by fluorescent detection to determine which enzyme-substrate combinations are dissociated; thus, identifying active inhibitors.

A rapid diagnostic assay can also be developed using the same microarray and the organism specific RNA oligomers used for the HTS screening assays. To use the assay, a subsample of the specimen extract is applied to the microarray after which the microarray is rinsed and analyzed with fluorescence detection. If a particular spot fluoresces then the sample is positive for the organism corresponding to that spot. The arrangement of the oligomer substrates on the microarray can be arranged depending on the particular application of the diagnostic assay.

Culture media containing each organism is extracted to release the proteins from the organisms. A subsample of this extract is applied to each grid on the microarray containing RNA oligomers. The microarray is rinsed with distilled water and analyzed with a standard laboratory fluorometer. Those spots corresponding to the specific organism should fluoresce. This process can be repeated for each organism to confirm selectivity and specificity. Finally, sensitivity testing can be conducted by repeating these assays using cultures with decreasing numbers of plaque forming units and/or extract dilutions.

What is claimed is:

1. A method of identifying an inhibitor of tRNA-target molecule binding, comprising: forming a mixture of a first nucleic acid molecule comprising a tRNA T.PSI.C-loop fragment, a target molecule capable of binding to the tRNA T.PSI.C-loop fragment, and a test compound, wherein the tRNA T.PSI.C-loop fragment contains at least one modified nucleotide; incubating the mixture under conditions that allow binding of the tRNA T.PSI.C-loop fragment and the target molecule in the absence of the test compound; and detecting whether or not the test compound inhibits the binding of the tRNA T.PSI.C-loop fragment and the target molecule, wherein the absence of binding of the tRNA fragment and the target molecule is indicative of the test compound being an inhibitor of tRNA-target molecule binding.

2. The method of claim 1, wherein the mixture further comprises a second nucleic acid molecule comprising an anticodon stem-loop fragment, wherein the target molecule is capable of binding to the tRNA T.PSI.C-loop fragment and the ASL fragment.

3. The method of claim 2, wherein the anticodon stem-loop contains at least one modified nucleotide.

4. The method of claim 2, wherein the first and second nucleic acid molecules are linked on a single nucleic acid molecule.

5. The method of claim 1, wherein the target molecule is selected from the group consisting of a nucleic acid molecule, a polypeptide, an antibody, a ligand, a carbohydrate, and a protein.

6. The method of claim 5, wherein the target molecule is a protein selected from the group consisting of an aminoacyl synthetase, a methyl transferase, and a pseudouridine synthase.

7. The method of claim 5, wherein the target molecule is a nucleic acid molecule selected from the group consisting of a ribosomal RNA, a tRNA and a viral RNA.

8. The method of claim 1, wherein the tRNA T.PSI.C-loop fragment contains at least one modified nucleotide at a position selected from a nucleotide corresponding to positions 53, 54, or 57 of a tRNA.

9. The method of claim 1, wherein the tRNA T.PSI.C-loop fragment comprises a modified nucleotide selected from the group consisting of ribothymidine, m1A, and Psi.

10. The method of claim 9, wherein the tRNA T.PSI.C-loop fragment comprises a nucleic acid molecule having the sequence 5'-h'i'j'k'l'(ribothymidine)(Psi) CN(m1A) NNl"k"j"i"h", wherein h'i'j'k'l' is complementary to l"k"j"i"h", where h', i', j', k', l', l", k", j", i", and h" are any nucleotide, and N is any nucleotide.

11. The method of claim 1, wherein the nucleic acid molecule is attached to a microarray.

12. A method of identifying an inhibitor of tRNA-target molecule interaction, comprising: forming a mixture comprising a first nucleic acid molecule comprising a tRNA D-loop fragment, a target molecule capable of binding to the tRNA D-loop fragment, and a test compound, wherein the tRNA D-loop fragment contains at least one modified nucleotide; incubating the mixture under conditions that allow binding of the tRNA D-loop fragment and the target molecule in the absence of the test compound; and detecting whether or not the test compound inhibits the binding of the tRNA D-loop fragment and the target molecule, wherein the absence of binding of the tRNA fragment and the target molecule is indicative of the test compound being an inhibitor of tRNA-target molecule interaction.

13. The method of claim 12, wherein the mixture further comprises a second nucleic acid molecule comprising an anticodon stem-loop fragment, wherein the target molecule is capable of binding to the tRNA T.PSI.C-loop fragment and the ASL fragment.

14. The method of claim 13, wherein the anticodon stem-loop contains at least one modified nucleotide.

15. The method of claim 13, wherein the first and second nucleic acid molecules are linked on a single nucleic acid molecule.

16. The method of claim 12, wherein the target molecule is selected from the group consisting of a nucleic acid molecule, a polypeptide, an antibody, a ligand, a carbohydrate, and a protein.

17. The method of claim 16, wherein the target molecule is a protein selected from the group consisting of an aminoacyl synthetase, a methyl transferase, and a pseudouridine synthase.

18. The method of claim 16, wherein the target molecule is a nucleic acid molecule selected from the group consisting of a ribosomal RNA, a tRNA and a viral RNA.

19. The method of claim 12, wherein the tRNA D-loop fragment contains at least one modified nucleotide at a position selected from a nucleotide corresponding to positions 16 or 19 of a tRNA.

20. The method of claim 12, wherein the tRNA D-loop fragment comprises at least one dihydrouridine.

21. The method of claim 12, wherein the tRNA D-loop fragment comprises a nucleotide molecule having the sequence 5'-m'n'o'p'NN(dihydrouridine) NN(dihydrouridine)NNp"o"n"m", wherein m', n', o', p', m", n", o", and p" are any nucleotide and m', n', o', and p' are complementary to m", n", o", and p", respectively, and N is any nucleotide.

22. The method of claim 12, wherein the nucleic acid molecule is attached to a microarray.

23. A method of diagnosing whether a subject has a bacterial infection, comprising: forming a mixture comprising a first nucleic acid molecule derived from a fragment of a tRNA molecule comprising at least one modified nucleotide and a biological sample from a subject, wherein the fragment tRNA molecule corresponds to a T.PSI.C-loop, a D-loop, or an anticodon stem loop structure; incubating the mixture under conditions that allow binding of the first nucleic acid molecule and a target molecule indicative of the presence of a bacteria in the absence of the test compound; and detecting whether the first nucleic acid molecule binds to the target molecule, wherein the binding of the first nucleic acid molecule and the target molecule is indicative of the positive diagnosis of a bacterial infection in the biological sample.

24. The method of claim 23, wherein the first nucleic acid molecule comprises a nucleic acid molecule derived from a bacterial Lys-tRNA.

25. The method of claim 24, wherein the bacterial Lys-tRNA is derived from a Category B bacteria.

26. The method of claim 23, wherein the target molecule is selected from the group consisting of a nucleic acid molecule, a polypeptide, an antibody, a ligand, a carbohydrate, and a protein.

27. The method of claim 26, wherein the target molecule is a protein selected from the group consisting of an aminoacyl synthetase, a methyl transferase, and a pseudouridine synthase.

28. The method of claim 26, wherein the target molecule is a nucleic acid molecule selected from the group consisting of a ribosomal RNA, a tRNA and a viral RNA.

29. The method of claim 23, wherein the nucleic acid molecule is attached to a microarray.

30. A method of identifying a target molecule that binds to a RNA molecule, comprising: forming a mixture comprising a biological sample and at least one nucleic acid molecule derived from or corresponding to a tRNA loop having at least one modified nucleotide, wherein the tRNA loop is selected from the group consisting of a T.PSI.C-loop, a D-loop, and an anticodon loop, incubating the mixture under conditions that allow binding of a target molecule in the biological sample to the first nucleic acid molecule, detecting whether a target molecule binds to the first nucleic acid molecule.

31. The method of claim 30, wherein the mixture comprises at least two nucleic acid molecules derived from a tRNA loop having at least one modified nucleotide.

32. The method of claim 30, wherein the biological sample is derived from a bacterial cell, a viral cell, a fungal cell, or an animal cell.

33. The method of claim 30, wherein the at least one nucleic acid molecule has the nucleic acid sequence 5'-h'i'j'k'l' (ribothymidine)(Psi) CN(m1A)NNl"k"j"i"h", wherein h'i'j'k'l' is complementary to l"k"j"i"h", where h', i', j', l', l", k", j", i", and h" are any nucleotide, and N is any nucleotide.

34. The method of claim 30, wherein the at least one nucleic acid molecule has the sequence 5'-m'n'o'p'NN(dihydrouridine) NN(dihydrouridine)NNp"o"n"m", wherein m', n', o', p', m", n", o", and p" are any nucleotide and m', n', o', and p' are complementary to m", n", o", and p", respectively, and N is any nucleotide.

35. The method of claim 30, wherein the at least one nucleic acid molecule has the sequence 5'-a'b'c'd'e'NUXNNYNe"(or Z)d"c"b"a"; wherein X, Y, and Z refer to modified nucleotides; a', b', c', d', e', a", b', c", d", and e" refer to any nucleotide and a', b', c', d', and e' are complementary to a", b", c", d", and e", respectively, and N refers to any nucleotide.

36. The method of claim 30, wherein the at least one nucleic acid molecule has the sequence 5'-$N^1N^2N^3N^4$(mcm5s2U)$N^6N^7$(ms2t6A)$N^9$(pseudouridine)$N^{11}N^{12}$, where $N^1$, $N^2$, $N^3$, $N^4$, $N^5$, $N^7$, $N^9$, $N^{11}$, and $N^{12}$ refer to any nucleotide.

37. The method of claim 30, wherein the biological sample comprises a target molecule that binds to the at least one nucleic acid molecule, wherein the target molecule is selected from the group consisting of a protein, a peptide, a nucleic acid molecule, an enzyme, an antibody, a ligand, or a carbohydrate.

38. The method of claim 30, wherein the at least one nucleic acid molecule is attached to a microarray.

39. The method of claim 30, wherein the at least one nucleic acid molecule is detectably labeled.

* * * * *